(12) United States Patent
Rothbaum

(10) Patent No.: US 11,642,343 B2
(45) Date of Patent: May 9, 2023

(54) METHODS OF TREATING SPLENOMEGALY

(71) Applicant: Telios Pharma, Inc., Redwood City, CA (US)

(72) Inventor: Wayne Philip Rothbaum, Delray Beach, FL (US)

(73) Assignee: Telios Pharma, Inc., Redwood City, CA (US)

( * ) Notice: Subject to any disclaimer, the term of this patent is extended or adjusted under 35 U.S.C. 154(b) by 0 days.

(21) Appl. No.: 17/565,579

(22) Filed: Dec. 30, 2021

(65) Prior Publication Data

US 2022/0184069 A1 Jun. 16, 2022

Related U.S. Application Data

(62) Division of application No. 17/623,927, filed as application No. PCT/US2021/012696 on Jan. 8, 2021.

(60) Provisional application No. 62/958,632, filed on Jan. 8, 2020.

(51) Int. Cl.
*A61K 31/4985* (2006.01)
*A61P 35/00* (2006.01)

(52) U.S. Cl.
CPC .......... *A61K 31/4985* (2013.01); *A61P 35/00* (2018.01)

(58) Field of Classification Search
None
See application file for complete search history.

(56) References Cited

U.S. PATENT DOCUMENTS

2016/0122365 A1   5/2016   Castro et al.

FOREIGN PATENT DOCUMENTS

| WO | 2015/057992 A1 | 4/2015 | |
|---|---|---|---|
| WO | 2016/024230 A1 | 2/2016 | |
| WO | WO 2019/243223 A1 * | 12/2019 | .......... C07D 401/12 |
| WO | 2021/097213 A1 | 5/2021 | |
| WO | 2021/142257 A1 | 7/2021 | |

OTHER PUBLICATIONS

Taneja et al., Leukemia & Lymphoma (2019), 60(2), pp. 519-522.*
International Search Report issued in related International Patent Application No. PCT/US2021/012696 dated Apr. 16, 2021.
Wang et al., "Spleens of myelofibrosis patients contain malignant hematopoietic stem cells," The Journal of Clinical Investigation, 122 (11): 3888-3899 (2012).
Tissino et al., "Functional and clinical relevance of VLA-4 (CD49d/CD29) in ibrutinib-treated chronic lymphocytic leukemia," Journal of Experimental Medicine, 215 (2): 681-697 (2018).
Wang et al., "Targeting BTK with Ibrutinib in Relapsed or Refractory Mantle-Cell Lymphoma," The New England Journal of Medicine, 369 (6): 507-516 (2013).
Rosti et al., "The expression of CXCR4 is down-regulated on the CD34+ cells of patients with myelofibrosis with myeloid metaplasia," Blood Cells, Molecules, and Diseases, 38: 280-286 (2007).
Dargart et al., "Dasatinib therapy results in decreased B cell proliferation, splenomegaly, and tumor growth in a murine model of lymphoma expressing Myc and Epstein-Barr virus LMP2A," Antiviral Research, 95: 49-56 (2012).
Ashangari et al., "Hairy Cell Leukemia Variant," Blood, 132 (Supplement 1): 5562 (2018).

* cited by examiner

*Primary Examiner* — Brian J Davis
(74) *Attorney, Agent, or Firm* — Morgan, Lewis & Bockius LLP

(57) ABSTRACT

Therapeutic methods and pharmaceutical compositions for treating splenomegaly in a human subject are described. In certain embodiments, the invention includes therapeutic methods of treating splenomegaly using a BTK inhibitor.

33 Claims, 5 Drawing Sheets

METHODS OF TREATING SPLENOMEGALY

FIELD OF THE INVENTION

Methods of treating splenomegaly using a Bruton's Tyrosine Kinase (BTK) inhibitor are disclosed herein.

BACKGROUND OF THE INVENTION

Myelofibrosis (MF) is a chronic leukemia, a cancer that affects the blood-forming tissues in the body. Myelofibrosis belongs to a group of diseases called myeloproliferative disorders and is an uncommon type of bone marrow cancer that disrupts the normal production of blood cells. Myelofibrosis causes extensive scarring in bone marrow, leading to severe anemia that can cause weakness and fatigue and it can also cause a low number of platelets, which increases the risk of bleeding. Myelofibrosis often causes an enlarged spleen and lymph nodes due to the accumulation of CD34+ malignant myeloid cells in the spleen.

The clinical spectrum of MF includes primary myelofibrosis and MF that develops during essential thrombocythemia or polycythemia vera. Myelofibrosis is a chronic hematologic malignancy characterized by splenomegaly, leukoerythroblastosis, cytopenias, teardrop poikilocytosis, marrow fibrosis, extramedullary hematopoiesis, increased marrow microvessel density, and constitutive mobilization of hematopoietic stem cells (HSC) and progenitor cells (HPC) that express CD34.

Myelofibrosis is also characterized by abnormal trafficking and homing of HSC and HPC in the bone marrow and peripheral blood, resulting in their constitutive mobilization and the establishment of splenomegaly. CXCR4-CXCL12 (CXCL12 also known as SDF-1) signaling plays a critical role in a variety of processes underlying proper lymphoid and myeloid cell development and function, including development and retention of precursor cells in the bone marrow, homing of immature and mature cells to secondary lymphoid organs and trafficking and homing of plasma cells to the bone marrow. In MF, the constitutive mobilization of HSC and HPC has been associated with profound alterations in the CXCR4-CXCL12 axis, which occur because of downregulation of CXCR4 expression by myelofibrotic CD34+ cells due to hypermethylation of the CXCR4 promoter, and the proteolytic degradation of CXCL12. In the spleen of MF patients, CXCL12 and integrins such as Very Late Antigen-4 (VLA-4) are highly expressed and CXCL12 acts as a chemoattractant for the mobilized CD34+ cells. This contrasts with the bone marrow and peripheral blood, where CXCL12 expression levels are abnormally low. Drawn to the spleen via CXCL12, adhesion molecules such as VLA-4 and its ligand VCAM-1 (vascular cell adhesion molecule 1) sequester the CD34+ cells, resulting in the formation of splenomegaly. In addition, this aberrant stem cell behavior can be influenced, not only by intrinsic properties of the stem cells, but also by regulatory signals provided by the MF microenvironment (Wang (2015) Experimental Hematology 43, 100-109). Therefore, the ability to manipulate cell trafficking, homing and sequestering via these pathways represents an opportunity to treat MF patients.

Bruton's Tyrosine Kinase is a non-receptor tyrosine kinase that belongs to the Tec family and has an important function in several benign and malignant cells of the hematopoietic system. Moreover, recent clinical studies with irreversible oral BTK inhibitors, acalabrutinib and ibrutinib, have demonstrated excellent clinical activity and tolerability against a variety of B-cell malignancies including: chronic lymphocytic leukemia (CLL), mantle cell lymphoma (MCL), Waldenstrom macroglobulinemia and diffuse large B-cell lymphoma. Furthermore, it is now clear the mechanism of action of BTK inhibitors is multifactorial, with a significant component of its function in lymphoid malignancies involving the disruption of the tumor cell and the microenvironment that protects it. Inhibition of BTK has been shown to regulate CLL, MCL and malignant myeloid cell migration in acute myeloid leukemia by inhibiting CXCR4-CXCL12 induced cell trafficking, homing and integrin adhesion by downregulating expression of numerous vascular adhesion molecules (Zaitseva (2014) Oncotarget 5, 9930-9938). CXCL12 plays a central role in CLL pathogenesis and progression, by regulating CLL cell interaction with the stromal microenvironment, leading to cell survival and proliferation. BTK has a role in signal transduction activated by the CXCR4-CXCL12 signaling axis and is involved in rapid integrin activation. BTK inhibition prevents CXCL12-induced triggering of Lymphocyte function-associated antigen-1 (LFA-1) and VLA-4 integrins. Furthermore, BTK inhibition blocks the activation of the small GTP-binding protein RhoA, controlling integrin affinity. Very importantly, BTK tyr-phosphorylation and activation by CXCL12 depends on upstream activation of JAK2 (Janus kinase 2). Thus, BTK and JAK protein tyrosine kinases manifest a hierarchical activity both in chemokine and integrin activation and dependent cell adhesion (Montresor (2018) Oncotarget, 9, 35123-35140). Lastly, BTK is highly expressed on both mature and primitive myeloid cells; including HSC and HPC. The CXCR4-CXCL12 signaling axis is a critical means of mobilization and homing for CD34+ cells.

At present, ruxolitinib, fedratinib and allogeneic stem cell transplantation are the primary means of treating patients with MF. Ruxolitinib, a drug that was developed to inhibit the JAK2 mutation, is often the first treatment used. It is also effective in people who have the CALR (calreticulin, located on chromosome 19p13.2) or MPL (myeloproliferative leukemia virus oncogene; located on chromosome 1p34) mutations because they also activate JAK2. It is effective in reducing spleen size and controlling symptoms and may increase overall survival, but it does not reverse fibrosis in most cases and can lead to anemia and low platelet counts. Surprisingly, ruxolitnb works equally as well in reducing splenomegaly and controlling symptoms in MF patients lacking the JAK2V617 driver mutation; confounding initial therapeutic expectations. However, ruxolitinib is not disease modifying because it has no effect on reducing the malignant CD34+ cell numbers or the Jak allele burden. Nonetheless, with a better understanding of the cellular and molecular events that lead to the development of MF, the possibility exists for safer and more efficacious targeted therapies, such as BTK inhibitors, to treat myeloproliferative neoplasms with splenomegaly through the modulation of cell trafficking, homing and adhesion.

SUMMARY OF THE INVENTION

The invention relates to a method of treating splenomegaly in a human subject in need thereof comprising administering a Bruton's Tyrosine Kinase inhibitor to the human subject. In some embodiments, the human subject has an accumulation of malignant CD34+ myeloid cells in the spleen. In some embodiments, the malignant CD34+ myeloid cells have decreased expression of CXCR4 relative to normal myeloid cells. In some embodiments, the human subject is suffering from myelofibrosis. In some embodiments, the myelofibrosis is selected from the group consisting of primary myelofibrosis, (PMF), post-polycythemia vera myelofibrosis (post PV-MF), and post-essential thrombocythemia myelofibrosis (post ET-MF). In some embodiments, the human subject did not respond to ruxolitinib therapy. In some embodiments, the human subject has a JAK2V617F mutation and optionally has acute myeloid leukemia (AML) secondary to a myeloproliferative neoplasm (MPN). In some embodiments, the human subject does not have a JAK2V617F mutation and optionally has acute myeloid leukemia secondary to a myeloproliferative neoplasm.

In some embodiments, the BTK inhibitor is administered in an amount sufficient to stimulate migration of the malignant CD34+ myeloid cells to peripheral blood of the human subject. In some embodiments, the BTK inhibitor is administered in an amount sufficient to stimulate apoptosis of the malignant CD34+ myeloid cells in the spleen of the human subject. In some embodiments, the BTK inhibitor is administered in an amount sufficient to decrease activity of VLA-4 in the malignant CD34+ myeloid cells. In some embodiments, the BTK inhibitor is administered in an amount sufficient to decrease expression of VLA-4 in the malignant CD34+ myeloid cells.

The invention also relates to a method of stimulating migration of malignant CD34+ myeloid cells from the spleen to the peripheral blood in a human subject suffering from splenomegaly, comprising administering a BTK inhibitor to the human subject. In some embodiments, the human subject has an accumulation of malignant CD34+ myeloid cells in the spleen. In some embodiments, the method encompasses stimulating apoptosis of malignant CD34+ myeloid cells in the spleen by administering a BTK inhibitor. In some embodiments, the malignant CD34+ myeloid cells have decreased expression of CXCR4 relative to normal myeloid cells. In some embodiments, the human subject is suffering from myelofibrosis. In some embodiments, the myelofibrosis is selected from the group consisting of primary myelofibrosis, post-polycythemia vera myelofibrosis, and post-essential thrombocythemia myelofibrosis. In some embodiments, the human subject did not respond to ruxolitinib therapy. In some embodiments, the human subject has a JAK2V617F mutation and optionally has acute myeloid leukemia secondary to a myeloproliferative neoplasm. In some embodiments, the human subject does not have a JAK2V617F mutation and optionally has acute myeloid leukemia secondary to a myeloproliferative neoplasm.

The methods of the invention encompass treatment of the human subject who has not been treated with a JAK2 inhibitor. The methods of the invention also encompass treatment of the human subject who is intolerant to a JAK2 inhibitor. The methods of the invention encompass treatment of the human subject who is ineligible for treatment with a JAK2 inhibitor. The methods of the invention encompass treatment of the human subject who is relapsed following JAK2 inhibitor treatment or is refractory to JAK2 inhibitor treatment.

In the methods of the invention, the BTK inhibitor is administered once daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, 480 mg and 560 mg.

In the methods of the invention, the BTK inhibitor is administered twice daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, 480 mg and 560 mg.

In the methods of the invention, the BTK inhibitor is orally administered.

In the methods of the invention, the BTK inhibitor is a covalent BTK inhibitor.

In the methods of the invention, the BTK inhibitor is a non-covalent BTK inhibitor.

DETAILED DESCRIPTION OF THE INVENTION

Figure 1A:
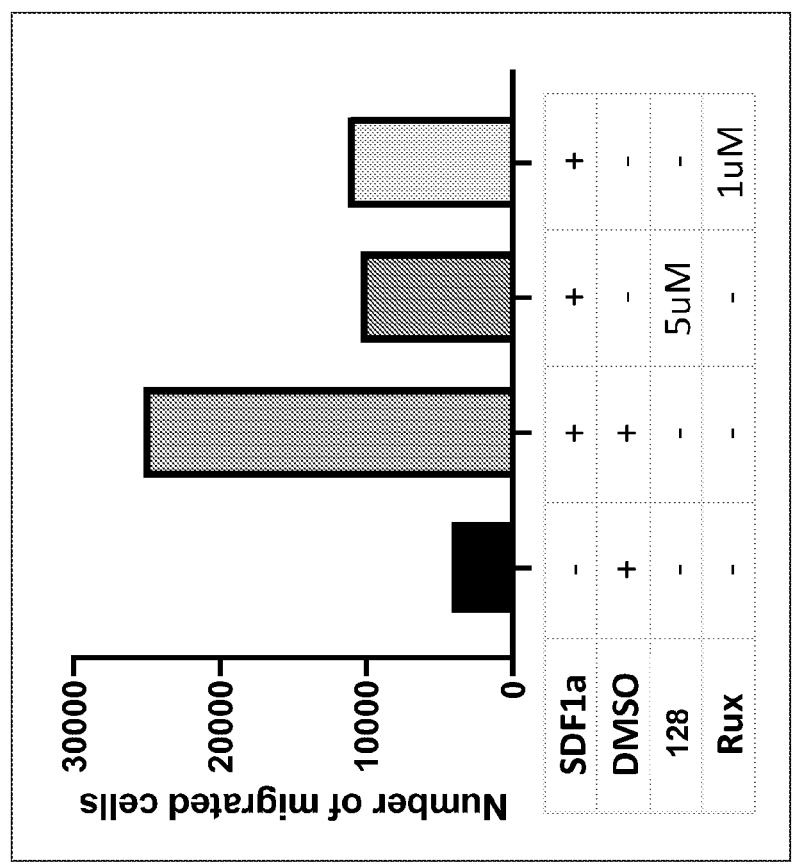
FIGS. 1A and 1B are graphs showing inhibition of cell migration towards SDF-1.

While preferred embodiments of the invention are shown and described herein, such embodiments are provided by way of example only and are not intended to otherwise limit the scope of the invention. Various alternatives to the described embodiments of the invention may be employed in practicing the invention.

Unless defined otherwise, all technical and scientific terms used herein have the same meaning as is commonly understood by one of skill in the art to which this invention belongs.

The terms "administered in combination with" and "co-administration" as used herein, encompass administration of two or more active pharmaceutical ingredients to a subject so that both agents and/or their metabolites are present in the subject at the same time. Co-administration includes simultaneous administration in separate compositions, administration at different times in separate compositions, or administration in a composition in which two or more agents are present.

The term "effective amount" or "therapeutically effective amount" or "amount sufficient" refers to that amount of an active pharmaceutical ingredient or combination of active pharmaceutical ingredients as described herein that is sufficient to effect the intended application including, but not limited to, disease treatment. A therapeutically effective amount may vary depending upon the intended application (in vitro or in vivo), or the subject and disease condition being treated (e.g., the weight, age and gender of the subject), the severity of the disease condition, the manner of administration, and other factors which can readily be determined by one of ordinary skill in the art. The term also applies to a dose that will induce a particular response in target cells, (e.g., malignant CD34+ myeloid cells). The specific dose will vary depending on the particular compounds chosen, the dosing regimen to be followed, whether the compound is administered in combination with other compounds, timing of administration, the tissue to which it is administered, and the physical delivery system in which the compound is carried.

"Myelofibrosis" refers to spontaneous scarring (fibrosis) of the bone marrow that disrupts the normal production of blood cells, leading to severe anemia and enlargement of the spleen, lymph nodes and liver. It can be associated with a variety of diseases, primarily myeloproliferative (preleukemic) disorders. It is also known as agnogenic myeloid metaplasia. Myelofibrosis, as used herein, includes but is not limited to, primary myelofibrosis, post-polycythemia vera myelofibrosis, and post-essential thrombocythemia myelofibrosis. Myelofibrosis as used herein, is characterized by accumulation of malignant CD34+ myeloid cells in the bone marrow, spleen and lymph nodes.

"Pharmaceutically acceptable carrier" or "pharmaceutically acceptable excipient" is intended to include any and all solvents, dispersion media, coatings, antibacterial and antifungal agents, isotonic, and absorption delaying agents. The use of such media and agents for active pharmaceutical ingredients is well known in the art. Except insofar as any conventional media or agent is incompatible with the active pharmaceutical ingredient, its use in the therapeutic compositions of the invention is contemplated. Supplementary active ingredients can also be incorporated into the described compositions.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In selected embodiments, the pharmaceutically acceptable base addition salt is chosen from ammonium, potassium, sodium, calcium, and magnesium salts. The term "cocrystal" refers to a molecular complex derived from a number of cocrystal formers known in the art. Unlike a salt, a cocrystal typically does not involve proton transfer between the cocrystal and the drug, and instead involves intermolecular interactions, such as hydrogen bonding, aromatic ring stacking, or dispersive forces, between the cocrystal former and the drug in the crystal structure.

The terms "QD," "qd," or "q.d." means quaque die, once a day, or once daily. The terms "BID," "bid," or "b.i.d." mean bis in die, twice a day, or twice daily. The terms "TID," "tid," or "t.i.d." mean ter in die, three times a day, or three times daily. The terms "QID," "qid," or "q.i.d." mean quater in die, four times a day, or four times daily.

The term "splenomegaly" as used herein refers to an enlargement of the spleen, measured by size or weight. In some embodiments, the enlargement is due to sequestration of malignant CD34+ myeloid cells and the resulting extramedullary hemopoiesis which develops.

A "therapeutic effect" as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

When ranges are used herein to describe, for example, physical or chemical properties such as molecular weight or chemical formulae, all combinations and subcombinations of ranges and specific embodiments therein are intended to be included. Use of the term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments such as, for example, an embodiment of any composition of matter, method or process that "consist of" or "consist essentially of" the described features.

BTK inhibitor compounds of the invention also include crystalline and amorphous forms of the any of the compounds in Table 1, including, for example, polymorphs, pseudopolymorphs, solvates, hydrates, unsolvated polymorphs (including anhydrates), conformational polymorphs, and amorphous forms of the compounds, as well as mixtures thereof. "Crystalline form" and "polymorph" are intended to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to.

Methods of Treating Complications of Myelofibrosis

The present disclosure relates to the discovery that a BTK inhibitor can be used to treat various complications of myelofibrosis including, for example, splenomegaly, extramedullary hematopoiesis and fibrosis. Accordingly, in certain aspects, the disclosure relates to methods for treating splenomegaly, extramedullary hematopoiesis and fibrosis by administering to a human subject in need thereof an effective amount of a BTK inhibitor, optionally in combination of one or more other supportive therapies or active agents for treating splenomegaly. The disclosure herein demonstrates that desirable therapeutic agents may be selected on the basis of BTK inhibition. Therefore, while not wishing to be bound to a particular mechanism of action, it is expected that BTK inhibition alters one or more downstream signaling components (e.g., CXCR-4, CXCL12, VLA-4, VCAM-1) to mobilize migration of CD34+ cells into the peripheral blood and will useful in the treatment of complications associated with myelofibrosis, particularly in treating or preventing one or more myelofibrosis complications including, but not limited to, splenomegaly, extramedullary hematopoiesis and fibrosis.

The present invention thus relates to a method of treating spenomegaly comprising the step of administering to a human in need thereof a BTK inhibitor compound selected from Table 1 or a pharmaceutically acceptable salt thereof. Tn some embodiments, the splenomegaly is secondary to myelofibrosis. In some embodiments, the MF is primary myelofibrosis, also known as chronic idiopathic myelofibrosis (cIMF). This is in contrast with myelofibrosis that develops secondary to polycythemia vera or essential thrombocythaemia. In some embodiments, however, the invention encompasses treating splenomegaly due to myelofibrosis that develops secondary to polycythemia vera or essential thrombocythaemia. In some embodiments, the BTK inhibitor is any of the compounds in Table 1 or a pharmaceutically acceptable salt thereof.

The present invention also relates to a method of treating a splenomegaly comprising the step of administering to a human in need thereof a BTK inhibitor or a pharmaceutically acceptable salt thereof. In an embodiment, the splenomegaly is in a human subject suffering from myelofibrosis selected from the group consisting of primary myelofibrosis, secondary myelofibrosis, myelofibrosis secondary to polycythemia vera (PV), myelofibrosis secondary to essential thrombocythemia (ET), myelofibrosis secondary to chronic myeloid leukemia (CML), and idiopathic myelofibrosis. In an embodiment, the myelofibrosis is selected from the group consisting of primary myelofibrosis, post-polycythemia vera myelofibrosis, and post-essential thrombocythemia myelofibrosis. In an embodiment, the primary myelofibrosis is selected from the group consisting of pre-fibrotic/early stage PMF and overt fibrotic stage PMF. In an embodiment, the human is determined as hydroxyurea (HU) intolerant (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly.

In an embodiment, the human subject is JAK2 inhibitor naïve (i.e. has never received therapy with a JAK2 inhibitor. In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any myeloproliferative neoplasm in a human subject receiving ruxolitinib or fedratinib, or (ii) a relapse of any myelofibrosis in a human subject following ruxolitinb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib therapy is a relapse of any myelofibrosis in a human subject following ruxolitinb or fedratinib therapy. In an embodiment, the BTK inhibitor is the compound selected from Table 1 and pharmaceutically acceptable salts thereof.

In an embodiment, the invention relates to a method of treating splenomegaly in a human that comprises the step of administering to said human a therapeutically effective amount of a BTK inhibitor or a pharmaceutically acceptable salt thereof, wherein the BTK inhibitor is a compound selected from Table 1.

In an embodiment, the invention relates to a method of treating extramedullary hematopoiesis in a human that comprises the step of administering to said human a therapeutically effective amount of a BTK inhibitor or a pharmaceutically acceptable salt thereof, wherein the BTK inhibitor is a compound selected from Table 1.

In an embodiment, the invention relates to a method of treating fibrosis in a human that comprises the step of administering to said human a therapeutically effective amount of a BTK inhibitor or a pharmaceutically acceptable salt thereof, wherein the BTK inhibitor is a compound selected from any of Table 1.

In an embodiment, the human subject has an accumulation of malignant CD34+ myeloid cells in their spleen. These malignant CD34+ myeloid cells have decreased expression of CXCR4 relative to normal myeloid cells. In an embodiment, the BTK inhibitor is administered in an therapeutically effective amount sufficient to stimulate migration of the malignant CD34+ myeloid cells to peripheral blood of the human subject. In an embodiment, the BTK inhibitor is administered in an amount sufficient to inactivate VLA-4 in the malignant CD34+ myeloid cells.

In an embodiment the invention relates to a method of stimulating migration of malignant CD34+ myeloid cells from the spleen to the peripheral blood in a human subject suffering from myelofibrosis, comprising administering a BTK inhibitor to the human subject. In an embodiment, the BTK inhibitor is administered in an amount sufficient to reduce activity of CXCR4 and CXCL12 thereby reducing the chemoattract effects these molecules on malignant CD34+ myeloid cells. The reduction of CXCR4 and CXCL12 activity contributes to the sequestration of malignant myeloid CD34+ cells in the spleen. In an embodiment, the the human subject has an accumulation of malignant CD34+ myeloid cells in their spleen. These malignant CD34+ myeloid cells have decreased expression of CXCR4 relative to normal myeloid cells.

In an embodiment, the method encompasses treating complications associated with myelofibrosis such as splenomegaly, extramedullary hematopoiesis and fibrosis, but not treating myelofibrosis itself (e.g. only the complications of myelofibrosis are treated in the human and not the myelofibrosis).

In an embodiment, the BTK inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 560 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the BTK inhibitor is administered to a human according to Section Dosages and Dosing Regimens.

In an embodiment, the human suffering from splenomegaly, extramedullary hematopoiesis or fibrosis has myelofibrosis which characterized by the presence of a CALR mutation (calreticulin, located on chromosome 19p13.2) in the human subject as described in Massie, New Engl. J. Med. (2013) 25, 2379-2390 and incorporated by reference herein in its entirety.

In an embodiment, the human suffering from splenomegaly, extramedullary hematopoiesis or fibrosis has myelofibrosis is characterized by the presence of an MPL mutation (myeloproliferative leukemia virus oncogene; located on chromosome 1p34) in the human subject as described in Pikman, Plos Med. (2006) 3, e270 and incorporated by reference herein in its entirety.

In an embodiment, the human suffering from splenomegaly, extramedullary hematopoiesis or fibrosis has myelofibrosis is characterized by JAK2V617F mutation in the human subject. JAK2V617F is a function mutation promoting cytokine-independent growth of myeloid cells, as described in Nakatake (Oncogene (2012) 31, 1323-1333) and incorporated by reference herein in its entirety.

In an embodiment, the human suffering from splenomegaly, extramedullary hematopoiesis or fibrosis has myelofibrosis characterized by one or more mutations selected from the group consisting of JAK2V617F, MPL, CALR and combinations thereof.

In an embodiment, the human suffering from splenomegaly, extramedullary hematopoiesis or fibrosis has myelofibrosis characterized by the absence of the JAK2V617F mutation.

In an embodiment, the invention relates to a method of treating splenomegaly in a human subject suffering from myelofibrosis secondary to essential thrombocythemia in a human that comprises the step of administering to said human a therapeutically effective amount of a BTK inhibitor or a pharmaceutically acceptable salt thereof, wherein the BTK inhibitor is a compound selected from Table 1.

In an embodiment, the invention relates to a method of treating myelofibrosis secondary to chronic myeloid leukemia in a human that comprises the step of administering to said human a therapeutically effective amount of a BTK inhibitor or a pharmaceutically acceptable salt thereof, wherein the BTK inhibitor is a compound selected from Table 1.

TABLE 1

BTK Inhibitors

| No. | IUPAC Name |
|---|---|
| 1. | Acalabrutinib ((S)-4-(8-amino-3-(1-(but-2-ynoyl)pyrrolidin-2-yl)imidazo[1,5-a]pyrazin-1-yl)-N-(pyridin-2-yl)benzamide) |
| 2. | Ibrutinib (1-[(3R)-3-[4-amino-3-(4-phenoxyphenyl)pyrazolo[3,4-d]pyrimidin-1-yl]piperidin-1-yl]prop-2-en-1-one) |
| 3. | (7S)-2-(4-phenoxyphenyl)-7-(1-prop-2-enoylpiperidin-4-yl)-4,5,6,7-tetrahydropyrazolo[1,5-a]pyrimidine-3-carboxamide |
| 4. | 2-(4-phenoxyphenyl)-7-(1-prop-2-enoylpiperidin-4-yl)-4,5,6,7-tetrahydropyrazolo[1,5-a]pyrimidine-3-carboxamide |
| 5. | 7 (R)-2-(4-phenoxyphenyl)-7-(1-prop-2-enoylpiperidin-4-yl)-4,5,6,7-tetrahydropyrazolo[1,5-a]pyrimidine-3-carboxamide |
| 6. | 6-amino-9-[(3R)-1-but-2-ynoylpyrrolidin-3-yl]-7-(4-phenoxyphenyl)purin-8-one |
| 7. | N-[3-[[5-fluoro-2-[4-(2-methoxyethoxy)anilino]pyrimidin-4-yl]amino]phenyl]prop-2-enamide |
| 8. | 10-[3-(hydroxymethyl)-4-[1-methyl-5-[[5-[(2S)-2-methyl-4-(oxetan-3-yl)piperazin-1-yl]pyridin-2-yl]amino]-6-oxopyridin-3-yl]pyridin-2-yl]-4,4-dimethyl-1,10-diazatricyclo[6.4.0.02,6]dodeca-2(6),7-dien-9-one |
| 9. | 1-[4-[[[6-amino-5-(4-phenoxyphenyl)pyrimidin-4-yl]amino]methyl]piperidin-1-yl]prop-2-en-1-one |
| 10. | 1-[4-[[[6-amino-5-(4-phenoxyphenyl)pyrimidin-4-yl]amino]methyl]piperidin-1-yl]prop-2-en-1-one |
| 11. | (2-chloro-4-phenoxyphenyl)-[4-[[(3R,6S)-6-(hydroxymethyl)oxan-3-yl]amino]-7H-pyrrolo[2,3-d]pyrimidin-5-yl]methanone |
| 12. | N-[3-[6-[4-[(2R)-1,4-dimethyl-3-oxopiperazin-2-yl]anilino]-4-methyl-5-oxopyrazin-2-yl]-2-methylphenyl]-4,5,6,7-tetrahydro-1-benzothiophene-2-carboxamide |
| 13. | 2-[2-[2-[4-[4-amino-3-(4-phenoxyphenyl)pyrazolo[3,4-d]pyrimidin-1-yl]piperidin-1-yl]ethoxy]ethoxy]-N-[2-(2,6-dioxopiperidin-3-yl)-1,3-dioxoisoindol-5-yl]acetamide |
| 14. | N-[3-[2-[4-(4-methylpiperazin-1-yl)anilino]furo[3,2-d]pyrimidin-4-yl]oxyphenyl]prop-2-enamide |
| 15. | 4-tert-butyl-N-[2-methyl-3-[1-methyl-5-[4-(morpholine-4-carbonyl)-3-(prop-2-enoylamino)anilino]-6-oxopyridin-3-yl]phenyl]benzamide |
| 16. | (R,E)-2-(3-(4-amino-3-(2-fluoro-4-phenoxyphenyl)-1H-pyrazolo[3,4-d]pyrimidin-1-yl)piperidine-1-carbonyl)-4-methyl-4-(4-(oxetan-3-yl)piperazin-1-yl)pent-2-enenitrile |
| 17. | (S)-4-(3-(but-2-ynamido)piperidin-1-yl)-5-fluoro-2,3-dimethyl-1H-indole-7-carboxamide |
| 18. | 4-(tert-Butyl)-N-(2-methyl-3-(4-methyl-6-((4-(morpholine-4-carbonyl)phenyl)amino)-5-oxo-4,5-dihydropyrazin-2-yl)phenyl)benzamide |
| 19. | N-(1-(7H-Pyrrolo[2,3-d] pyrimidin-4-yl)piperidin-3-yl)-2-((3-chlorophenyl)amino)acetamide |
| 20. | 6-cyclopropyl-8-fluoro-2-[2-(hydroxymethyl)-3-[1-methyl-5-[[5-(4-methylpiperazin-1-yl)pyridin-2-yl]amino]-6-oxopyridin-3-yl]phenyl]isoquinolin-1-one |
| 21. | N-[5-[9-[4-(methanesulfonamido)phenyl]-2-oxobenzo[h][1,6]naphthyridin-1-yl]-2-methylphenyl]prop-2-enamide |
| 22. | 4-(4-((4-((3-acrylamidophenyl)amino)-5-fluoropyrimidin-2-yl)amino)phenoxy)-N-methylpicolinamide |
| 23. | (7S)-3-fluoro-4-[3-(8-fluoro-1-methyl-2,4-dioxoquinazolin-3-yl)-2-methylphenyl]-7-(2-hydroxypropan-2-yl)-6,7,8,9-tetrahydro-5H-carbazole-1-carboxamide |
| 24. | 1-[3-fluoro-4-[7-(5-methyl-1H-imidazol-2-yl)-1-oxo-2,3-dihydroisoindol-4-yl]phenyl]-3-[3-(trifluoromethyl)phenyl]urea |
| 25. | 9-(1-methylpyrazol-4-yl)-1-(1-prop-2-enoyl-2,3-dihydroindol-6-yl)benzo[h][1,6]naphthyridin-2-one |
| 26. | 7-(2-hydroxypropan-2-yl)-4-[2-methyl-3-(4-oxoquinazolin-3-yl)phenyl]-9H-carbazole-1-carboxamide |
| 27. | 10-[2-(Hydroxymethyl)-3-[1-methyl-6-oxo-5-(pyrimidin-4-ylamino)pyridin-3-yl]phenyl]-4,4-dimethyl-7-thia-10-azatricyclo[6.4.0.02,6]dodeca-1(8),2(6)-dien-9-one |
| 28. | (S)-5-amino-1-(1-cyanopiperidin-3-yl)-3-(4-(2,4-difluorophenoxy)phenyl)-1H-pyrazole-4-carboxamide |
| 29. | (S)-4-(3-(1-Acryloylpyrrolidin-2-yl)-8-aminoimidazo[1,5-a] pyrazin-1-yl)-N-(pyridin-2-yl)benzamide |
| 30. | (S,E)-4-(8-Amino-3-(1-(4-(dimethylamino)but-2-enoyl)pyrrolidin-2-yl)imidazo[1,5-a]pyrazin-1-yl)-N(pyridin-2-yl)benzamide |

TABLE 1-continued

BTK Inhibitors

| No. | IUPAC Name |
|---|---|
| 31. | (S)-4-(8-Amino-3-(1-but-2-ynoylpyrrolidin-2-yl)imidazo[1,5-a]pyrazin-1-yl)-N-(4-methylpyridin-2-yl)benzamide |
| 32. | (S,E)-4-(8-Amino-3-(1-(4-methoxybut-2-enoyl)pyrrolidin-2-yl)imidazo[1,5-a]pyrazin-1-yl)-N-(4-propylpyridin-2-yl)benzamide |
| 33. | (S)-4-(8-Amino-3-(1-but-2-ynoylpyrrolidin-2-yl)imidazo[1,5-a] pyrazin-1-yl)-N-(4-(trifluoromethyl)pyridin-2-yl)benzamide |
| 34. | (S)-4-(8-Amino-3-(1-but-2-ynoylpyrrolidin-2-yl)imidazo[1,5-a]pyrazin-1-yl)-N-(4,5,6,7-tetrahydrobenzo[d]thiazol-2-yl)benzamide |
| 35. | (S)-4-(3-(1-acryloylpyrrolidin-2-yl)-8-aminoimidazo[1,5-a] pyrazin-1-yl)-2-fluoro-N-(pyridin-2-yl)benzamide |
| 36. | (S)-4-(3-(1-Acryloylpyrrolidin-2-yl)-8-aminoimidazo[1,5-a]pyrazin-1-yl)-2-methoxy-N-(pyridin-2-yl)benzamide |
| 37. | (S,E)-4-(8-Amino-3-(1-(4-(dimethylamino)but-2-enoyl)pyrrolidin-2-yl)imidazo[1,5-a]pyrazin-1-yl)-N-(thiazol-2-yl)benzamide |
| 38. | (S)-4-(3-(1-Acryloylpiperidin-2-yl)-8-aminoimidazo[1,5-a] pyrazin-1-yl)-N-(4-fluoropyridin-2-yl)benzamide |
| 39. | (S)-4-(3-(1-Acryloylpiperidin-2-yl)-8-aminoimidazo[1,5-a] pyrazin-1-yl)-N-(4-cyanopyridin-2-yl)benzamide |
| 40. | (S)-4-(8-Amino-3-(1-(vinylsulfonyl)piperidin-2-yl)imidazo[1,5-a] pyrazin-1-yl)-N-(4-(trifluoromethyl)pyridin-2-yl)benzamide |
| 41. | (S)-4-(3-(1-Acryloylpiperidin-2-yl)-8-aminoimidazo[1,5-a] pyrazin-1-yl)-N-(pyrimidin-2-yl)benzamide |
| 42. | (S)-4-(3-(1-Acryloylpiperidin-2-yl)-8-aminoimidazo[1,5-a] pyrazin-1-yl)-N-(4-methylpyrimidin-2-yl)benzamide |
| 43. | (S)-4-(8-Amino-3-(1-but-2-ynoylpiperidin-2-yl)imidazo[1,5-a] pyrazin-1-yl)-N-(pyrimidin-4-yl)benzamide |
| 44. | (S)-4-(8-Amino-3-(1-but-2-ynoylpiperidin-2-yl)imidazo[1,5-a] pyrazin-1-yl)-N-(pyridazin-3-yl)benzamide |
| 45. | (S,E)-4-(8-Amino-3-(1-(4-methoxybut-2-enoyl)piperidin-2-yl)imidazo[1,5-a] pyrazin-1-yl)-N-(5-ethylthiazol-2-yl)benzamide |
| 46. | (S)-4-(3-(1-Acryloylpiperidin-2-yl)-8-aminoimidazo[1,5-a] pyrazin-1-yl)-2-fluoro-N-(4-propylpyridin-2-yl)benzamide |
| 47. | (S,E)-4-(8-Amino-3-(1-(4-(dimethylamino)but-2-enoyl)piperidin-2-yl)imidazo[1,5-a]pyrazin-1-yl)-2-methoxy-N-(4-propylpyridin-2-yl)benzamide |
| 48. | 4-(8-Amino-3-((S)-1-but-2-ynoylpiperidin-2-yl)imidazo[1,5-a] pyrazin-1-yl)-3-methyl-N-(pyridin-2-yl)benzamide |
| 49. | 4-(3-(Acrylamidomethyl)-8-aminoimidazo[1,5-a] pyrazin-1-yl)-N-(pyridin-2-yl)benzamide |
| 50. | (S)-4-(8-Amino-3-(1-but-2-ynamidoethyl)imidazo[1,5-a]pyrazin-1-yl)-N-(pyridin-2-yl)benzamide |
| 51. | (S)-S-2-(2-(8-Amino-1-(4-(pyridin-2-ylcarbamoyl)phenyl)imidazo[1,5-a]pyrazin-3-yl)pyrrolidin-1-yl)-2-oxoethylethanethioate |
| 52. | (S)-4-(8-Amino-3-(1-(4-hydroxy-4-methylpent-2-ynoyl)pyrrolidin-2-yl)imidazo[1,5-a]pyrazin-1-yl)-N(pyridin-2-yl)benzamide |
| 53. | (S)-4-(8-Amino-3-(1-(6-chloropyrimidine-4-carbonyl)pyrrolidin-2-yl)imidazo[1,5-a] pyrazin-1-yl)-N-(pyridin-2-yl)benzamide |
| 54. | (S)-4-(8-Amino-3-(1-pent-2-ynoylpyrrolidin-2-yl)imidazo[1,5-a] pyrazin-1-yl)-N-(pyridin-2-yl)benzamide |
| 55. | (S)-4-(8-Amino-3-(1-(3-cyclopropylpropioloyl)pyrrolidin-2-yl)imidazo[1,5-a] pyrazin-1-yl)-N-(pyridin-2-yl)benzamide |
| 56. | (S)-4-(8-Amino-3-(1-hex-2-ynoylpyrrolidin-2-yl)imidazo[1,5-a] pyrazin-1-yl)-N-(pyridin-2-yl)benzamide |
| 57. | 4-(3-(1-Acryloylazepan-2-yl)-8-aminoimidazo[1,5-a]pyrazin-1-yl)-N-(pyridin-2-yl)benzamide |
| 58. | (R)-4-(8-Amino-3-(4-but-2-ynoylmorpholin-3-yl)imidazo[1,5-a] pyrazin-1-yl)-N-(pyridin-2-yl)benzamide |
| 59. | (S)-4-(8-amino-3-(1-(N-methylbut-2-ynamido)ethyl)imidazo[1,5-a]pyrazin-1-yl)-N-(4-(trifluoromethyl)pyridin-2-yl)benzamide |
| 60. | (S)-4-(3-(1-acryloylpyrrolidin-2-yl)-8-aminoimidazo[1,5-a]pyrazin-1-yl)-N-(4-fluoropyridin-2-yl)benzamide |
| 61. | (S)-4-(3-(1-acryloylpyrrolidin-2-yl)-8-aminoimidazo[1,5-a]pyrazin-1-yl)-N-(4-(pyrrolidin-1-yl)pyridin-2-yl)benzamide |
| 62. | (S)-4-(8-amino-3-(1-but-2-ynoylpiperidin-2-yl)imidazo[1,5-a]pyrazin-1-yl)-N-(4-fluoropyridin-2-yl)benzamide |
| 63. | (S)-4-(8-amino-3-(1-but-2-ynoylpiperidin-2-yl)imidazo[1,5-a]pyrazin-1-yl)-N-(pyridine-2-yl)benzamide |
| 64. | (S)-4-(3-(1-acryloylpiperidin-2-yl)-8-aminoimidazo[1,5-a]pyrazin-1-yl)-N-(pyridine-2-yl)benzamide |
| 65. | (S)-4-(8-amino-3-(1-but-2-ynoylpyrrolidin-2-yl)imidazo[1,5-a]pyrazin-1-yl)-N-(4-propylpyridin-2-yl)benzamide |
| 66. | (S,E)-4-(8-amino-3-(1-(4-methoxy-N-methylbut-2-enamido)ethyl)imidazo[1,5-a]pyrazin-1-yl)-N-(4-propylpyridin-2-yl)benzamide |
| 67. | (S)-4-(8-amino-3-(1-(vinylsulfonyl)piperidin-2-yl)imidazo[1,5-a]pyrazin-1-yi)-N-(4-propylpyridin-2-yl)benzamide |
| 68. | (S)-4-(3-(1-acryloylpiperidin-2-yl)-8-aminoimidazo[1,5-a]pyrazin-1-yl)-N-(4-propylpyridin-2-yl)benzamide |

TABLE 1-continued

BTK Inhibitors

| No. | IUPAC Name |
|---|---|
| 69. | (S)-4-(3-(1-acryloylpyrrolidin-2-yl)-8-aminoimidazo[1,5-a]pyrazin-1-yl)-N-(4-(trifluoromethyl)pyridin-2-yl)benzamide |
| 70. | (S)-4-(8-amino-3-(1-but-2-ynoylpiperidin-2-yl)imidazo[1,5-a]pyrazin-1-yl)-N-(4-(trifluoromethyl)pyridin-2-yl)benzamide |
| 71. | (S)-4-(8-amino-3-(1-but-2-ynoylpiperidin-2-yl)imidazo[1,5-a]pyrazin-1-yl)-N-(4-propylpyridin-2-yl)benzamide |
| 72. | (S,E)-4-(8-amino-3-(1-(4-(dimethylamino)but-2-enoyl)pyrrolidin-2-yl)imidazo[1,5-a]pyrazin-1-yl)-N-(4-isopropylpyridin-2-yl)benzamide |
| 73. | 4-(8-amino-3-((S)-1-(vinylsulfonyl)piperidin-2-yl)imidazo[1,5-a]pyrazin-1-yl)-3-methyl-N-(pyridin-2-yl)benzamide |
| 74. | (S)-4-(8-amino-3-(1-but-2-ynoylpiperidin-2-yl)imidazo[1,5-a]pyrazin-1-yl)-2-fluoro-N-(4-propylpyridin-2-yl)benzamide |
| 75. | (S,E)-4-(8-amino-3-(1-(4-methoxy-N-methylbut-2-enamido)ethyl)imidazo[1,5-a]pyrazin-1-yl)-N-(4-(trifluoromethyl)pyridin-2-yl)benzamide |
| 76. | (S,E)-4-(8-amino-3-(1-(4-(dimethylamino)-N-methylbut-2-enamido)ethyl)imidazo[1,5-a]pyrazin-1-yl)-N-(4-propylpyridin-2-yl)benzamide |
| 77. | (S,E)-4-(8-amino-3-(1-(4-(pyrrolidin-1-yl)but-2-enoyl)pyrrolidin-2-yl)imidazo[1,5-a]pyrazin-1-yl)-N-(4-propylpyridin-2-yl)benzamide |
| 78. | (S,E)-4-(8-amino-3-(1-(4-(dimethylamino)but-2-enoyl)piperidin-2-yl)imidazo[1,5-a]pyrazin-1-yl)-N-(pyridin-2-yl)benzamide |
| 79. | (S)-4-(8-amino-3-(1-(2-chloropyrimidine-4-carbonyl)pyrrolidin-2-yl)imidazo[1,5-a]pyrazin-1-yl)-N-(4-propylpyridin-2-yl)benzamide |
| 80. | (S)-4-(3-(1-acrylamidoethyl)-8-aminoimidazo[1,5-a]pyrazin-1-yl)-N-(pyridin-2-yl)benzamide |
| 81. | (S)-4-(3-(1-acryloylpyrrolidin-2-yl)-8-aminoimidazo[1,5-a]pyrazin-1-yl)-N-(thiazol-2-yl)benzamide |
| 82. | (S)-4-(8-amino-3-(1-but-2-ynoylpyrrolidin-2-yl)imidazo[1,5-a]pyrazin-1-yl)-N-(4-isopropylpyridin-2-yl)benzamide |
| 83. | (S)-4-(8-amino-3-(1-(2-chloropyrimidine-4-carbonyl)piperidin-2-yl)imidazo[1,5-a]pyrazin-1-yl)-N-(4-propylpyridin-2-yl)benzamide |
| 84. | (S,E)-4-(8-amino-3-(1-(4-methoxybut-2-enoyl)piperidin-2-yl)imidazo[1,5-a]pyrazin-1-yl)-N-(4-(trifluoromethyl)pyridin-2-yl) benzamide |
| 85. | (S)-4-(3-(1-acryloylpiperidin-2-yl)-8-aminoimidazo[1,5-a]pyrazin-1-yl)-N-(4-(trifluoromethyl)pyridin-2-yl)benzamide |
| 86. | (S)-4-(8-amino-3-(1-but-2-ynoylpiperidin-2-yl)imidazo[1,5-a]pyrazin-1-yl)-2-methoxy-N-(4-propylpyridin-2-yl)benzamide |
| 87. | ()-4-(8-amino-3-(1-(4-methoxybut-2-enoyl)piperidin-2-yl)imidazo[1,5-a]pyrazin-1-yl)-2-methoxy-N-(4-propylpyridin-2-yl) benzamide |
| 88. | (S)-4-(8-amino-3-(1-(2-chloropyrimidine-4-carbonyl)piperidin-2-yl)imidazo[1,5-a]pyrazin-1-yl)-N-(4-(trifluoromethyl)pyridin-2-yl)benzamide |
| 89. | (S)-4-(8-amino-3-(1-but-2-ynoylpiperidin-2-yl)imidazo[1,5-a]pyrazin-1-yi)-N-(5-ethylthiazol-2-yl)benzamide |
| 90. | (S)-4-(3-(1-acryloylpiperidin-2-yl)-8-aminoimidazo[1,5-a]pyrazin-1-yl)-N-(5-ethylthiazol-2-yl)benzamide |
| 91. | (S)-4-(8-amino-3-(1-(2-chloropyrimidine-4-carbonyl)piperidin-2-yl)imidazo[1,5-a]pyrazin-1-yl)-N-(5-ethylthiazol-2-yl)benzamide |
| 92. | (R,E)-4-(8-amino-3-(4-(4-methoxybut-2-enoyl)morpholin-3-yl)imidazo[1,5-a]pyrazin-1-yl)-N-(pyridin-2-yl)benzamide |
| 93. | (S,E)-4-(8-amino-3-(1-(4-methoxybut-2-enoyl)piperidin-2-yl)imidazo[1,5-a]pyrazin-1-yl)-N-(4-propylpyridin-2-yl)benzamide |
| 94. | (S)-4-(3-(1-acryloylpyrrolidin-2-yl)-8-aminoimidazo[1,5-a]pyrazin-1-yl)-N-(4-cyanopyridin-2-yl)benzamide |
| 95. | (S)-4-(8-amino-3-(1-but-2-ynoylpyrrolidin-2-yl)imidazo[1,5-a]pyrazin-1-yl)-N-(4-methoxypyridin-2-yl)benzamide |
| 96. | (S)-4-(3-(1-acryloylpyrrolidin-2-yl)-8-aminoimidazo[1,5-a]pyrazin-1-yl)-N-(4-methylpyridin-2-yl)benzamide |
| 97. | (S)-4-(3-(1-acryloylpyrrolidin-2-yl)-8-aminoimidazo[1,5-a]pyrazin-1-yl)-N-(4-propylpyridin-2-yl)benzamide |
| 98. | (S)-4-(3-(1-acryloylpyrrolidin-2-yl)-8-aminoimidazo[1,5-a]pyrazin-1-yl)-N-(4-ethylpyridin-2-yl)benzamide |
| 99. | (S,E)-4-(8-amino-3-(1-(4-(dimethylamino)but-2-enoyl)pyrrolidin-2-yl)imidazo[1,5-a]pyrazin-1-yl)-N-(pyridin-2-yl)benzamide |
| 100. | (S,E)-4-(8-amino-3-(1-(4-methoxybut-2-enoyl)pyrrolidin-2-yl)imidazo[1,5-a]pyrazin-1-yl)-N-(4-(trifluoromethyl)pyridin-2-yl)benzamide |
| 101. | (S)-4-(8-amino-3-(1-(2-chloropyrimidine-4-carbonyl)pyrrolidin-2-yl)imidazo[1,5-a]pyrazin-1-yl)-N-(4-methylpyridin-2-yl)benzamide |
| 102. | (S)-4-(8-amino-3-(1-but-2-ynoylpyrrolidin-2-yl)imidazo[1,5-a]pyrazin-1-yl)-N-(4-cyanopyridin-2-yl)benzamide |
| 103. | (S)-4-(8-amino-3-(1-but-2-ynoylpyrrolidin-2-yl)imidazo[1,5-a]pyrazin-1-yl)-N-(4-ethylpyridin-2-yl)benzamide |
| 104. | (S)-4-(8-amino-3-(1-but-2-ynoylpyrrolidin-2-yl)imidazo[1,5-a]pyrazin-1-yl)-N-(4-phenylpyridin-2-yl)benzamide |
| 105. | (S)-4-(3-(1-acryloylpyrrolidin-2-yl)-8-aminoimidazo[1,5-a]pyrazin-1-yi)N-(4-phenylpyridin-2-yl)benzamide |
| 106. | (R,E)-1-(3-(4-amino-3-(4-phenoxyphenyl)-1H-pyrazolo[3,4-d]pyrimidin-1-yl)piperidin-1-yl)-4-(dimethylamino)but-2-en-1-one |

TABLE 1-continued

BTK Inhibitors

| No. | IUPAC Name |
|---|---|
| 107. | (E)-1-(3-(4-amino-3-(4-phenoxyphenyl)-1H-pyrazolo[3,4-d]pyrimidin-l-yl)piperidin-l-yl)-4-morpholinobut-2-en-1-one |
| 108. | 1-(4-(4-amino-3-(4-phenoxyphenyl)-1H-pyrazolo[3,4-d]pyrimidin-1-yl)piperidin-1-yl)prop-2-en-1-one |
| 109. | (E)-1-(4-(4-amino-3-(4-phenoxyphenyl)-1H-pyrazolo[3,4-d]pyrimidin-l-yl)piperidin-l-yl)-4-(dimethylamino)but-2-en-l-one |
| 110. | (E)-N-((ls,4s)-4-(4-amino-3-(4-phenoxyphenyl)-1H-pyrazolo[3,4-d]pyrimidin-l-yl)cyclohexyl)-4-(dimethylamino)but-2-enamide |
| 111. | 1-(4-(4-amino-3-(4-phenoxyphenyl)-1H-pyrazolo[3,4-d]pyrimidin-1-yl)piperidin-1-yl)prop-2-en-1-one |
| 112. | N-((lr,4r)-4-(4-amino-3-(4-phenoxyphenyl)-1H-pyrazolo[3,4-d]pyrimidin-l-yl)cyclohexyl)acrylamide |
| 113. | (E)-1-((R)-2-((4-amino-3-(4-phenoxyphenyl)-1H-pyrazolo[ 3,4-d]pyrimidin-l-yl)methyl)pyrolidin-l-yl)-4-(dimethylamino)but-2-en-l-one |
| 114. | (E)-1-((S)-2-((4-amino-3-(4-phenoxyphenyl)-1H-pyrazolo[3,4-d]pyrimidin-l-yl)methyl)pyrolidin-l-yl)-4-(dimethylamino)but-2-en-l-one |
| 115. | l-((R)-2-((4-amino-3-(4-phenoxyphenyl)-1H-pyrazolo[3,4-d]pyrimidin-l-yl)methyl)pyrrolidin-l-yl)prop-2-en-l-one |
| 116. | l-((S)-2-((4-amino-3-(4-phenoxyphenyl)-1H-pyrazolo[3,4-d]pyrimidin-l-yl)methyl)pyrrolidin-l-yl)prop-2-en-l-one |
| 117. | 1 ((R)-2-((4-amino-3-(4-phenoxyphenyl)-1H-pyrazolo[3,4-d]pyrimidin-l-yl)methyl)pyrrolidin-l-yl)but-2-yn-lone |
| 118. | 1-((S)-2-((4-amino-3-(4-phenoxyphenyl)-1H-pyrazolo[3,4-d]pyrimidin-l-yl)methyl)pyrrolidin-l-yl)but-2-yn-l-one |
| 119. | l-((R)-3-(4-amino-3-(4-phenoxyphenyl)-1H-pyrazolo[ 3,4-d]pyrimidin-l-yl)piperidin-l-yl)but-2-yn-l-one |
| 120. | (E)-N-((lr,4r)-4-(4-amino-3-(4-phenoxyphenyl)-1H-pyrazolo[3,4-d]pyrimidin-l-yl)cyclohexyl-4-(dimethylamino)but-2-enamide |
| 121. | N-(2-(4-amino-3-(4-phenoxyphenyl)-1H-pyrazolo[3,4-d]pyrimidin-l-yl)ethyl)-N-methylacrylamide |
| 122. | (E)-1-(4-(4-amino-3-(4-phenoxyphenyl)-1H-pyrazolo[3,4-d]pyrimidin-l-yl)-4-morpholinobut-2-en-1-one |
| 123. | (E)-1-((S-2-((4-amino-3-(4-phenoxyphenyl)-1H-pyrazolo[3,4-d]pyrimidin-lyl)methyl)pyrrolidin-l-yl)-4-morpholinobut-2-en-l-one |
| 124. | N-((ls,4s)-4-(4-amino-3-(4-phenoxyphenyl)-1H-pyrazolo[3,4-d]pyrimidin-l-yl)cyclohexyl)but-2-ynamide |
| 125. | N-(2-(4-amino-3-(4-phenoxyphenyl)-1H-pyrazolo[3,4-d]pyrimidin-l-yl)ethyl)acrylamide |
| 126. | (E)-1-((R)-3-(4-amino-3-(4-phenoxyphenyl)-1H-pyrazolo[3,4-d]pyrimidin-l-yl)piperidin-l-yl)-4-morpholinobut-2-en-l-one |
| 127. | (E)-N-((ls,4s)-4-(4-amino-3-(4-phenoxyphenyl)-1H-pyrazolo[3,4-d]pyrimidin-l-yl)cyclohexyl)-4-morpholinobut-2-enamide |
| 128. | 1-(4-(((6-amino-5-(4-phenoxyphenyl)pyrimidin-4-yl)amino)methyl)-4-fluoropiperidin-1-yl)prop-2-en-1-one |
| 129. | N-[3-[[5-fluoro-2-[4-(2-methoxyethoxy)anilino]pyrimidin-4-yl]amino]phenyl]prop-2-enamid |
| 130. | 6-amino-9-[(3R)-1-but-2-ynoylpyrrolidin-3-yl]-7-(4-phenoxyphenyl)purin-8-one |
| 131. | (7S)-2-(4-phenoxyphenyl)-7-(1-prop-2-enoylpiperidin-4-yl)-4,5,6,7-tetrahydropyrazolo[1,5-a]pyrimidine-3-carboxamide |

In some embodiments, the BTK inhibitor is TG-1701 or Loxo-305.

In an embodiment, the invention relates to a method of treating myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MF is selected from the group consisting of myelofibrosis, primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF.

In an embodiment, the invention relates to a method of treating myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID, wherein the MF is selected from the group consisting of MF secondary to polycythemia vera, MF secondary to essential thrombocythemia and MF secondary to CML.

In an embodiment, the invention relates to a method of treating primary myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating post-polycythemia vera myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating post-essential thrombocythemia myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a use of a BTK inhibitor or a pharmaceutically acceptable salt thereof, in the manufacture of a medicament for treating myelofibrosis comprises the step of administering to a human one or more doses of a BTK inhibitor compound from Table 1 or a pharmaceutically acceptable salt thereof. In an embodiment, the MF is selected from the group consisting of primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF.

In an embodiment, the invention relates to a use of a BTK inhibitor or a pharmaceutically acceptable salt thereof, in the manufacture of a medicament for treating primary myelofibrosis, wherein the treating comprises the step of administering to a human one or more doses of a BTK inhibitor compound from Table 1 or a pharmaceutically acceptable salt thereof.

In an embodiment, the invention relates to a use of a BTK inhibitor or a pharmaceutically acceptable salt thereof, in the manufacture of a medicament for treating post-polycythemia vera myelofibrosis, wherein the treating comprises the step of administering to a human one or more doses of a BTK inhibitor compound selected from Table 1 or a pharmaceutically acceptable salt thereof.

In an embodiment, the invention relates to a use of a BTK inhibitor or a pharmaceutically acceptable salt thereof, in the manufacture of a medicament for treating post-essential thrombocythemia myelofibrosis, wherein the treating comprises the step of administering to a human one or more doses of a BTK inhibitor compound selected from Table 1 or a pharmaceutically acceptable salt thereof.

In an embodiment, the invention relates to a use of a BTK inhibitor or a pharmaceutically acceptable salt thereof, in the manufacture of a medicament for treating myleofibrosis secondary to polycythemia vera, wherein the treating comprises the step of administering to a human one or more doses of a BTK inhibitor compound from Table 1 or a pharmaceutically acceptable salt thereof.

In an embodiment, the invention relates to a use of a BTK inhibitor or a pharmaceutically acceptable salt thereof, in the manufacture of a medicament for treating myleofibrosis secondary to essential thrombocythemia, wherein the treating comprises the step of administering to a human one or more doses of a BTK inhibitor compound selected from Table 1 or a pharmaceutically acceptable salt thereof.

In an embodiment, the invention relates to a use of a BTK inhibitor or a pharmaceutically acceptable salt thereof, in the manufacture of a medicament for treating myleofibrosis secondary to chronic myeloid leukemia, wherein the treating comprises the step of administering to a human one or more doses of a BTK inhibitor compound selected from Table 1 or a pharmaceutically acceptable salt thereof.

In an embodiment, the invention relates to a use of a composition comprising a BTK inhibitor selected from Table 1 or a pharmaceutically acceptable salt thereof, in the manufacture of a medicament for treating myleofibrosis comprising the step of administering to a human one or more doses of the composition comprising the BTK inhibitor or a pharmaceutically acceptable salt thereof. In an embodiment, the myelofibrosis is selected from the group consisting of primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF.

The methods described above may be used as first-line cancer therapy, or after treatment with conventional therapy, including ruxolitinib or fedratinib.

A BTK inhibitor or a pharmaceutically acceptable salt thereof may also be used in combination with radiation therapy, hormone therapy, surgery and immunotherapy, which therapies are well known to those skilled in the art, for treating myleofibrosis selected from the group consisting of primary myelofibrosis, idiopathic myelofibrosis, post-polycythemia vera myelofibrosis, and post-essential thrombocythemia myelofibrosis. In an embodiment, the primary myelofibrosis is selected from the group consisting of pre-fibrotic/early stage PMF and overt fibrotic stage PMF.

Mechanism of Action

Myelofibrosis is characterized by the constitutive mobilization of hematopoietic stem cells and progenitor cells and the establishment of extramedullary hematopoiesis (EMH). Both splenic and peripheral blood myelofibroid CD34+ cells equally share a defective ability to home to the bone marrow, but not the spleen. This trafficking pattern cannot be attributed to discordant expression of integrins or chemokine receptors other than the down-regulation of CXCR4 by both peripheral blood and splenic CD34+ cells. The concentration of the intact chemoattractant, CXCL12 (the ligand for CXCR4) is greater in splenic myelofibrosis plasma than peripheral blood myelofibrosis plasma. Functionally inactive truncated products of CXCL12 which are the product of proteolytic degradation by serine proteases were detected at similar levels in both splenic and peripheral blood myelofibrotic plasma. The myelofibrotic splenic microenvironment is characterized by increased levels of intact, functional CXCL12, which contributes to the localization of malignant CD34+ myeloid cells to the spleen (Wang (2015) Exp. Hematol. 43, 100-109).

Abnormal CD34+ cell trafficking and extramedullary hematopoiesis are integral components of the pathobiology of myelofibrosis. The constitutive mobilization of malignant myeloid CD34+ cells is accounted for by the downregulation of CXCR4 on these cells and a reduction of the amount of intact CXCL12, which serves as a chemoattractant for CD34+ cells. An increased concentration of intact, fully functional CXCL12 within the myelofibrotic spleen, but not in peripheral blood, and, presumably, in bone marrow contributes to the homing of malignant myeloid CD34+ cells to the spleens rather than to the bone marrow of myelofibrosis patients, ultimately leading to extramedullary hematopoiesis in the spleen. The initial establishment of extramedullary hematopoiesis in myelofibrosis patients is in part due to the presence of intact CXCL12 in normal spleens, the production of which has been localized to cells lining vessels. As myelofibrosis progresses, the marrow is progressively depleted of CD34+ cells, but CD34+ cells are present in the peripheral blood, which is a result of CD34+ cell trafficking between the myelofibrotic spleen, peripheral blood, and marrow (Wang (2015) Exp. Hematol. 43, 100-109).

Disease progression in myelofibrosis is frequently accompanied by greater degrees of splenomegaly due to increased extramedullary hematopoiesis. For EMH to occur, a permissive microenvironment must be established which supplies the signals that are required for myelofibrotic hematopoietic stem cells to enter the spleen and then initiate and sustain hematopoiesis. Alterations within the microenvironment of the spleen contribute to the abnormal trafficking of myelofibrotic stem cells (MF-SC) leading to the development of EMH. Splenic myelofibrosis plasma is characterized by increased concentrations of CXCL12, which results in the initiation and development of EMH in myelofibrosis patients. The splenic cells responsible for the excessive production of CXCL12 appear to be endothelial cells. The microenvironment within the marrow and spleen differ in myelofibrosis in part due to the increased levels of intact CXCL12 present in the spleen. These different microenvironments within the bone marrow and spleen contribute to sequestration of malignant CD34+ myeloid cells in the spleen and subsequent disease progression (Wang (2015) Exp. Hematol. 43, 100-109).

Reduced CXCR4 in the peripheral blood and bone marrow releases malignant CD34+ cells from the marrow, while high CXCL12 levels attract malignant CD34+ myeloid cells to the spleen, while low levels of CXCL12 in peripheral blood promote sequestration in spleen. This results in accumulation of malignant CD34+ myeloid cells to the spleen and depletes the bone marrow of CD34+ myeloid cells. Inhibition of BTK reduces expression and activity of CXCL12, thus the chemoattractant effects of CXCL12 which result in accumulation of malignant CD34+ myeloid cells in the spleen is reduced. This inhibition of CXCL12 in the spleen results in migration of the malignant CD34+ myeloid cells to from the spleen to the peripheral blood, effectively reducing the formation of myelofibrotic tissue in the spleen.

The concentration of soluble VCAM-1, a degradation product of VCAM-1, is elevated in the plasma of patients with primary myelofibrosis and is correlated with the absolute numbers of CD34+ cells in the peripheral blood of patients with primary myelofibrosis. Furthermore, CXCR-4 expression by CD34+ cells is downregulated and plasma CXCL12 levels are elevated, which accounts for altered CLCL12/CXCR-4 interactions leading to CD34+ cell mobilization. The constitutive mobilization of myelofibrotic HSC and HPC has been associated with profound alterations in the CXCR4/CXCL12 axis, which occur as a consequence of down-regulation of CXCR4 expression by myelofibrotic CD34+ cells due to hypermethylation of the CXCR4 promoter and the proteolytic degradation of CXCL12 and vascular adhesion molecule-1 (VCAM-1). Drugs that target the proteases responsible for constitutive CD34+ cell mobilization present an intriguing strategy to prevent the establishment of or to eliminate extramedullary sites of hematopoiesis in patients with primary myelofibrosis.

Transmigration of leukocytes and of progenitor cells is crucial to the process of extramedullary hematopoiesis. As mentioned above, this process is regulated by chemokines such as CXCL12 and is also mediated by the integrins LFA1 and VLA4. JAKV617F, but not mutated CALR stimulates integrin signaling via activation of the small GTPase Rap1, resulting in increased binding of granulocytes to ICAM-1 and VCAM-1 (abundantly expressed in spleen). Differences in chemotaxis in concert with differential integrin binding of JAKV617F versus CALR mutated leukocytes can contribute to extramedullary hematopoiesis. In primary myelofibrosis, the risk of splenomegaly is less pronounced in CALR-mutated patients than in JAKV617F-positive individuals. JAK2V617F kinase, via its signaling intermediates BTK, P13K/AKT, PLCy1, and RhoA, collaborates with chemokine CXCL12 and regulates cell migration. This mechanism provides rationale for the contribution of these downstream molecules in abnormal cell motility of JAKV617F-positive myeloid progenitors and stem cells migrating from bone marrow to peripheral blood and to extramedullary organs. Thus, the use of BTK inhibitors to inhibit abnormal migration and homing of the JAKV617F-positive clone in MPN is encompassed in the invention. In some embodiments, however, the presence of the JAKV617F-positive clone does not impact the treatment with a BTK inhibitor. Thus, BTK inhibitor treatment of human subjects both with the JAKV617F mutation, and without the JAKV617F mutation are encompassed in the invention.

Methods of Treating Myelofibrosis

The present invention relates to a method of treating myelofibrosis comprising the step of administering to a human in need thereof a BTK inhibitor compound selected from Table 1 or a pharmaceutically acceptable salt thereof. In some embodiments, the MF is primary myelofibrosis, also known as chronic idiopathic myelofibrosis. This is in contrast with myelofibrosis that develops secondary to polycythemia vera or essential thrombocythaemia. In some embodiments, however, the invention encompasses treating myelofibrosis that develops secondary to polycythemia vera or essential thrombocythaemia. In some embodiments, the BTK inhibitor is any of the compounds in Table 1 or a pharmaceutically acceptable salt thereof.

The present invention also relates to a method of treating a myelofibrosis comprising the step of administering to a human in need thereof a BTK inhibitor or a pharmaceutically acceptable salt thereof. In an embodiment, the myelofibrosis is selected from the group consisting of primary myelofibrosis, secondary myelofibrosis, myelofibrosis secondary to polycythemia vera, myelofibrosis secondary to essential thrombocythemia, myelofibrosis secondary to chronic myeloid leukemia, and idiopathic myelofibrosis. In an embodiment, the myelofibrosis is selected from the group consisting of primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF. In an embodiment, the human is determined as hydroxyurea intolerant (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly.

In an embodiment, the human subject is JAK2 inhibitor naïve (i.e. has never received therapy with a JAK2 inhibitor. In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any MPN in a human subject receiving ruxolitinib or fedratinib, or (ii) a relapse of any myelofibrosis in a human subject following ruxolitinb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib therapy is a relapse of any myelofibrosis in a human subject following ruxolitinb or fedratinib therapy. In an embodiment, the BTK inhibitor is the compound selected from Table 1 and pharmaceutically acceptable salts thereof.

In an embodiment, the invention relates to a method of treating primary myelofibrosis in a human that comprises the step of administering to said human a therapeutically effective amount of a BTK inhibitor or a pharmaceutically acceptable salt thereof, wherein the BTK inhibitor is a compound selected from Table 1. In some embodiments, the BTK inhibitor is a covalent or irreversibile BTK inhibitor. In some embodiments, the BTK inhibitor is a non-covalent or reversible BTK inhibitor.

In an embodiment, the invention relates to a method of treating post-polycythemia vera myelofibrosis in a human that comprises the step of administering to said human a therapeutically effective amount of a BTK inhibitor or a pharmaceutically acceptable salt thereof, wherein the BTK inhibitor is a compound selected from Table 1.

In an embodiment, the invention relates to a method of treating post-essential thrombocythemia myelofibrosis in a human that comprises the step of administering to said human a therapeutically effective amount of a BTK inhibitor or a pharmaceutically acceptable salt thereof, wherein the BTK inhibitor is a compound selected from any of Table 1.

In an embodiment, the human subject has an accumulation of malignant CD34+ myeloid cells in their spleen. These malignant CD34+ myeloid cells have decreased expression of CXCR4 relative to normal myeloid cells. In an embodiment, the BTK inhibitor is administered in an therapeutically effective amount sufficient to stimulate migration of the malignant CD34+ myeloid cells to peripheral blood from the bone marrow or spleen of the human subject. In an embodiment, the BTK inhibitor is administered in an amount sufficient to inactivate VLA-4 in the malignant CD34+ myeloid cells.

In an embodiment the invention relates to a method of stimulating migration of malignant CD34+ myeloid cells from the spleen to the peripheral blood in a human subject suffering from myelofibrosis, comprising administering a BTK inhibitor to the human subject. In an embodiment, the the human subject has an accumulation of malignant CD34+ myeloid cells in their spleen. These malignant CD34+ myeloid cells have decreased expression of CXCR4 relative to normal myeloid cells.

In an embodiment, the present invention relates to a method of treating secondary myelofibrosis comprising the step of administering to a human in need thereof a BTK inhibitor, wherein the BTK inhibitor is a compound selected from Table 1 or a pharmaceutically acceptable salt thereof, wherein the secondary myelofibrosis is selected from the group consisting of myelofibrosis secondary to polycythemia vera, and myelofibrosis secondary to essential thrombocythemia. In an embodiment, the polycythemia vera is phlebotomy-dependent polycythemia vera. In an embodiment, the human subject is determined as hydroxyurea intolerance (unacceptable side effects). In an embodiment, the human subject is determined as hydroxyurea resistant (inadequate response). In an embodiment, the human subject has splenomegaly. In an embodiment, the human has splenomegaly and is phlebotomy-dependent. In an embodiment, the human subject is phlebotomy-dependent without splenomegaly. In an embodiment, the human subject has failed previous MF therapy with ruxolitinib or fedratinib.

In an embodiment, the BTK inhibitor is administered in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 560 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the BTK inhibitor is administered to a human according to Section Dosages and Dosing Regimens.

In an embodiment, myelofibrosis is selected from primary myelofibrosis, post-polycythemia vera myelofibrosis, and post-essential thrombocythemia myelofibrosis. In an embodiment, the myelofibrosis is selected from primary myelofibrosis, post-polycythemia vera myelofibrosis, and post-essential thrombocythemia myelofibrosis, and the human subject failed ruxolitinib or fedratinib therapy for PMF, post PV-MF or post ET-MF.

In an embodiment, the myelofibrosis is characterized by the presence of a CALR mutation.

In an embodiment, the myelofibrosis is characterized by the presence of an MPL mutation.

In an embodiment, the myelofibrosis is characterized by JAK2V617F mutation in the human subject.

In an embodiment, the myelofibrosis is characterized by one or more mutations selected from the group consisting of JAK2V617F, MPL, CALR and combinations thereof.

In an embodiment, the invention relates to a method of treating myelofibrosis secondary to polycythemia vera in a human that comprises the step of administering to said human a therapeutically effective amount of a BTK inhibitor or a pharmaceutically acceptable salt thereof, wherein the BTK inhibitor is a compound selected from Table 1.

In an embodiment, the invention relates to a method of treating myelofibrosis secondary to essential thrombocythemia in a human that comprises the step of administering to said human a therapeutically effective amount of a BTK inhibitor or a pharmaceutically acceptable salt thereof, wherein the BTK inhibitor is a compound selected from Table 1.

In an embodiment, the invention relates to a method of treating myelofibrosis secondary to chronic myeloid leukemia in a human that comprises the step of administering to said human a therapeutically effective amount of a BTK inhibitor or a pharmaceutically acceptable salt thereof, wherein the BTK inhibitor is a compound selected from Table 1.

In an embodiment, the invention relates to a method of treating myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID. In an embodiment, the MF is selected from the group consisting of myelofibrosis, primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF.

In an embodiment, the invention relates to a method of treating myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID, wherein the MF is selected from the group consisting of MF secondary to polycythemia vera, MF secondary to essential thrombocythemia and MF secondary to CML.

In an embodiment, the invention relates to a method of treating primary myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating post-polycythemia vera myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a method of treating post-essential thrombocythemia myelofibrosis in a human that comprises the step of administering to said human a therapeutically effective amount of a BTK inhibitor compound selected from Table 1 or a pharmaceutically acceptable salt thereof, in a dosage selected from the group consisting of 15 mg QD, 25 mg QD, 30 mg QD, 50 mg QD, 60 mg QD, 75 mg QD, 90 mg QD, 100 mg QD, 120 mg QD, 150 mg QD, 175 mg QD, 180 mg QD, 200 mg QD, 225 mg QD, 240 mg QD, 250 mg QD, 275 mg QD, 300 mg QD, 325 mg QD, 350 mg QD, 360 mg QD, 375 mg QD, 480 mg QD, 15 mg BID, 25 mg BID, 30 mg BID, 50 mg BID, 60 mg BID, 75 mg BID, 90 mg BID, 100 mg BID, 120 mg BID, 150 mg BID, 175 mg BID, 180 mg BID, 200 mg BID, 225 mg BID, 240 mg BID, 250 mg BID, 275 mg BID, 300 mg BID, 325 mg BID, 350 mg BID, 360 mg BID, 375 mg BID, and 480 mg BID.

In an embodiment, the invention relates to a use of a BTK inhibitor or a pharmaceutically acceptable salt thereof, in the manufacture of a medicament for treating myleofibrosis comprises the step of administering to a human one or more doses of a BTK inhibitor compound from Table 1 or a pharmaceutically acceptable salt thereof. In an embodiment, the MF is selected from the group consisting of primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF.

In an embodiment, the invention relates to a use of a BTK inhibitor or a pharmaceutically acceptable salt thereof, in the manufacture of a medicament for treating primary myelofibrosis, wherein the treating comprises the step of administering to a human one or more doses of a BTK inhibitor compound from Table 1 or a pharmaceutically acceptable salt thereof.

In an embodiment, the invention relates to a use of a BTK inhibitor or a pharmaceutically acceptable salt thereof, in the manufacture of a medicament for treating post-polycythemia vera myelofibrosis, wherein the treating comprises the step of administering to a human one or more doses of a BTK inhibitor compound selected from Table 1 or a pharmaceutically acceptable salt thereof.

In an embodiment, the invention relates to a use of a BTK inhibitor or a pharmaceutically acceptable salt thereof, in the manufacture of a medicament for treating post-essential thrombocythemia myelofibrosis, wherein the treating comprises the step of administering to a human one or more doses of a BTK inhibitor compound selected from Table 1 or a pharmaceutically acceptable salt thereof.

In an embodiment, the invention relates to a use of a BTK inhibitor or a pharmaceutically acceptable salt thereof, in the manufacture of a medicament for treating myeleofibrosis secondary to polycythemia vera, wherein the treating comprises the step of administering to a human one or more doses of a BTK inhibitor compound from Table 1 or a pharmaceutically acceptable salt thereof.

In an embodiment, the invention relates to a use of a BTK inhibitor or a pharmaceutically acceptable salt thereof, in the manufacture of a medicament for treating myeleofibrosis secondary to essential thrombocythemia, wherein the treating comprises the step of administering to a human one or more doses of a BTK inhibitor compound selected from Table 1 or a pharmaceutically acceptable salt thereof.

In an embodiment, the invention relates to a use of a BTK inhibitor or a pharmaceutically acceptable salt thereof, in the manufacture of a medicament for treating myeleofibrosis secondary to chronic myeloid leukemia, wherein the treating comprises the step of administering to a human one or more doses of a BTK inhibitor compound selected from Table 1 or a pharmaceutically acceptable salt thereof.

In an embodiment, the invention relates to a use of a composition comprising a BTK inhibitor selected from Table 1 or a pharmaceutically acceptable salt thereof, in the manufacture of a medicament for treating myelofibrosis comprising the step of administering to a human one or more doses of the composition comprising the BTK inhibitor or a pharmaceutically acceptable salt thereof. In an embodiment, the myelofibrosis is selected from the group consisting of primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF.

The methods described above may be used as first-line cancer therapy, or after treatment with conventional therapy, including ruxolitinib or fedratinib.

A BTK inhibitor or a pharmaceutically acceptable salt thereof may also be used in combination with radiation therapy, hormone therapy, surgery and immunotherapy, which therapies are well known to those skilled in the art, for treating myeleofibrosis selected from the group consisting of primary myelofibrosis, idiopathic myelofibrosis, post-polycythemia vera myelofibrosis, and post-essential thrombocythemia myelofibrosis. In an embodiment, the primary myelofibrosis is selected from the group consisting of pre-fibrotic/early stage PMF and overt fibrotic stage PMF.

Methods of Treating Myeloproliferative Neoplasms

The present invention also relates to a method of treating a MPN comprising the step of administering to a human in need thereof a BTK inhibitor, or a pharmaceutically acceptable salt thereof. In an embodiment, the MPN is selected from the group consisting of polycythemia vera, myelofibrosis, primary myelofibrosis, thrombocythemia, essential thrombocythemia, idiopathic systemic mastocystosis (SM), chronic neutrophilic leukemia (CNL), chronic eosinophilic leukemia-not otherwise specified (CEL-NOS), unclassified myeloproliferative neoplasm (MPN-U), myelodysplastic syndrome (MDS), and systemic mast cell disease (SMCD).

In an embodiment, the MPN is selected from the group consisting of chronic neutrophilic leukemia (CNL), chronic eosinophilic leukemia, chronic myelomonocytic leukemia (CMML), atypical chronic myeloid leukemia (aCML), juvenile myelomonocytic leukemia (JMML), hypereosinophilic syndromes (HES), and myelodysplastic/myeloproliferative neoplasms with ring sideroblasts and thrombocytosis (MDS/MPN-RS-T). In an embodiment, the polycythemia vera is phlebotomy-dependent polycythemia vera. In an embodiment, the human is determined as hydroxyurea intolerance (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly.

In an embodiment, the human subject is JAK2 inhibitor naïve (i.e. has never received therapy with a JAK2 inhibitor. In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any MPN in a human subject receiving ruxolitinib or fedratinib, or (ii) a relapse of any myelofibrosis in a human subject following ruxolitinb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib therapy is a relapse of any myelofibrosis in a human subject following ruxolitinb or fedratinib therapy. In an embodiment, the BTK inhibitor is the compound selected from Table 1 and pharmaceutically acceptable salts thereof.

In an embodiment, the present invention relates to a method of treating a MPN comprising the step of administering to a human in need thereof a BTK inhibitor, wherein the BTK inhibitor is a compound selected from Table 1 or a pharmaceutically acceptable salt thereof, wherein the MPN is selected from the group consisting of polycythemia vera and essential thrombocythemia. In an embodiment, the polycythemia vera is phlebotomy-dependent polycythemia vera. In an embodiment, the human subject is determined as hydroxyurea intolerance (unacceptable side effects). In an embodiment, the human subject is determined as hydroxyurea resistant (inadequate response). In an embodiment, the human subject has splenomegaly. In an embodiment, the human has splenomegaly and is phlebotomy-dependent. In an embodiment, the human subject is phlebotomy-dependent without splenomegaly. In an embodiment, the human subject has failed previous MPN therapy with ruxolitinib or fedratinib.

The present invention also relates to a method of treating a blast phase MPN (MPN-BP) comprising the step of administering to a human in need thereof a BTK inhibitor, or a pharmaceutically acceptable salt thereof. In an embodiment, the MPN-BP is selected from the group consisting of blast phase polycythemia vera (BP-PV), blast phase myelofibrosis, blast phase blast phase thrombocythemia, blast phase essential thrombocythemia (BP-ET), blast phase systemic mastocystosis (BP-SM), blast phase chronic neutrophilic leukemia (BP-CNL), blast phase myelodysplastic syndrome (BP-MDS), and blast phase systemic mast cell disease (BP-SMCD). In an embodiment, the MPN-BP is selected from the group consisting of blast phase chronic neutrophilic leukemia (BP-CNL), blast phase chronic eosinophilic leukemia, blast phase chronic myelomonocytic leukemia (BP-CMML), blast phase atypical chronic myeloid leukemia (BP-aCML), blast phase juvenile myelomonocytic leukemia (BP-JMML), blast phase hypereosinophilic syndromes (BP-HES), and blast phase myelodysplastic/myeloproliferative neoplasms with ring sideroblasts and thrombocytosis (BP-MDS/MPN-RS-T). In an embodiment, the blast phase polycythemia vera is phlebotomy-dependent polycythemia vera. In an embodiment, the human is determined as hydroxyurea intolerance (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly.

In an embodiment, the human subject is JAK2 inhibitor naïve (i.e. has never received therapy with a JAK2 inhibitor. In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any MPN in a human subject receiving ruxolitinib or fedratinib, or (ii) a relapse of any myelofibrosis in a human subject following ruxolitinb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib therapy is a relapse of any myelofibrosis in a human subject following ruxolitinb or fedratinib therapy. In an embodiment, the BTK inhibitor is the compound selected from Table 1 and pharmaceutically acceptable salts thereof. In an embodiment, the BTK inhibitor is administered to a human according to Section Dosages and Dosing Regimens.

In an embodiment, the MPN is characterized by CALR mutation.

In an embodiment, the MPN is characterized by MPL mutation.

In an embodiment, the MPN is characterized by JAK2V617F mutation.

In an embodiment, the MPN is characterized by one or more mutations selected from the group consisting of JAK2V617F, MPL, CALR and mixtures thereof.

Combinations with BET Inhibitors

Bromodomain and extraterminal domain (BET) protein is a transcriptional regulator that is required for efficient expression of several growth promoting, anti-apoptotic genes, and cell cycle progression. BET family comprises BRD2, BRD3, BRD4 and BRDT. During transcription, BET proteins are recruited to the chromatin via the N-terminal bromodomains (BRD), in which this domain recognizes acetylated lysine residues in histone H3 and H4. Inhibitors of BET disrupt this BET-histone interaction and subsequently downregulates transcription of oncogenes including MYC.

MYC and BTK are important regulators of cellular processes and tumor progression. In light of the relationship between BET inhibition and MYC down-regulation and the relationship between overexpression of MYC and cancer, BET inhibitors are useful for treating MYC-associated diseases. Further, BET inhibitors in ation with BTK inhibitors are useful for treating myeloid cell diseases.

In some embodiments, the invention relates to a method of treating splenomegaly, extramedullary hematopoiesis or fibrosis by administering to a human subject in need thereof an effective amount of a BTK inhibitor in combination with a BET inhibitor. The disclosure herein demonstrates that desirable therapeutic agents may be selected on the basis of BTK inhibition and BET inhibition. Therefore, while not wishing to be bound to a particular mechanism of action, it is expected that BTK inhibition in combination with BET inhibition alters one or more downstream signaling components (e.g., CXCR-4, CXCL12, VLA-4, VCAM1) to mobilize migration of CD34+ cells into the peripheral blood and will useful in the treatment of complications associated with myelofibrosis, particularly in treating or preventing one or more myelofibrosis complications including, but not limited to, splenomegaly, extramedullary hematopoiesis or fibrosis.

The present invention thus relates to a method of treating splenomegaly, extramedullary hematopoiesis or fibrosis comprising the step of administering to a human in need thereof a BTK inhibitor compound selected from Table 1 or a pharmaceutically acceptable salt thereof in combination with a BET inhibitor compound selected from Table 2 or a pharmaceutically acceptable salt thereof. In some embodiments, the splenomegaly is secondary to myelofibrosis. In some embodiments, the splenomegaly is associated with primary myelofibrosis, also known as chronic idiopathic myelofibrosis. This is in contrast with myelofibrosis that develops secondary to polycythemia vera or essential thrombocythaemia. In some embodiments, however, the invention encompasses treating splenomegaly due to myelofibrosis that develops secondary to polycythemia vera or essential thrombocythaemia. In some embodiments, the BTK inhibitor is a compound selected from Table 1 or a pharmaceutically acceptable salt thereof in combination with a BET inhibitor compound selected from Table 2 or a pharmaceutically acceptable salt thereof. In an embodiment, the human is determined as hydroxyurea intolerant (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly.

In an embodiment, the human subject is JAK2 inhibitor naïve (i.e. has never received therapy with a JAK2 inhibitor. In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any MPN in a human subject receiving ruxolitinib or fedratinib, or (ii) a relapse of any myelofibrosis in a human subject following ruxolitnb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib therapy is a relapse of any myelofibrosis in a human subject following ruxolitnb or fedratinib therapy. In an embodiment, the BTK inhibitor is the compound selected from Table 1 and pharmaceutically acceptable salts thereof. In an embodiment, the human is suffering from splenomegaly, extramedullary hematopoiesis or fibrosis characterized by one or more mutations selected from the group consisting of JAK2V617F, MPL, CALR and combinations thereof.

In an embodiment, the human subject is JAK2 inhibitor naïve (i.e. has never received therapy with a JAK2 inhibitor). In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any MPN in a human subject receiving ruxolitinib or fedratinib, or (ii) a relapse of any myelofibrosis in a human subject following ruxolitnb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib

TABLE 2

BET Inhibitors

| No. | IUPAC Name |
|---|---|
| 1. | 2-[(4S)-6-(4-chlorophenyl)-1-methyl-4H-[1,2]oxazolo[5,4-d][2]benzazepin-4-yl]acetamide |
| 2. | Propan-2-Yl N-[(2s,4r)-1-Ethanoyl-2-Methyl-6-[4-[[8-(Oxidanylamino)-8-Oxidanylidene-Octanoyl]amino]phenyl]-3,4-Dihydro-2h-Quinolin-4-Yl]carbamate |
| 3. | 2-[(4S)-6-(4-chlorophenyl)-8-methoxy-1-methyl-4H-[1,2,4]triazolo[4,3-a][1,4]benzodiazepin-4-yl]-N-ethylacetamide |
| 4. | 7-(3,5-dimethyl-1,2-oxazol-4-yl)-8-methoxy-1-[(1R)-1-pyridin-2-ylethyl]-3H-imidazo[4,5-c]quinolin-2-one |
| 5. | tert-butyl 2-[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]acetate |
| 6. | tert-butyl 2-[(9R)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]acetate |
| 7. | 2-[(9S)-7-(4-chlorophenyl)-4,5,13-trimethyl-3-thia-1,8,11,12-tetrazatricyclo[8.3.0.0$^{2,6}$]trideca-2(6),4,7,10,12-pentaen-9-yl]-N-(4-hydroxyphenyl)acetamide |
| 8. | 2-methoxy-N-(3-methyl-2-oxo-1,2,3,4-tetrahydroquinazolin-6-yl)benzenesulfonamide |
| 9. | 2-[4-(2-hydroxyethoxy)-3,5-dimethylphenyl]-5,7-dimethoxy-3H-quinazolin-4-one |
| 10. | 2-(4-(2-Iisopropylamino)ethoxy)-3,5-dimethylphenyl)-5,7-dimethoxyquinazolin-4(3H)-on |

The present invention encompasses a method of treating myelofibrosis comprising the step of administering to a human in need thereof a BTK inhibitor compound selected from Table 1 or a pharmaceutically acceptable salt thereof in combination with a BET inhibitor selected from Table 2 or a pharmaceutically acceptable salt thereof. In some embodiments, the myelofibrosis is primary myelofibrosis, also known as chronic idiopathic myelofibrosis. This is in contrast with myelofibrosis that develops secondary to polycythemia vera or essential thrombocythaemia. In some embodiments, however, the invention encompasses treating myelofibrosis that develops secondary to polycythemia vera or essential thrombocythaemia. In some embodiments, the BTK inhibitor is a compound selected from Table 1 or a pharmaceutically acceptable salt thereof in combination with a a BET inhibitor compound selected from Table 2 or a pharmaceutically acceptable salt thereof. In an embodiment, the human is determined as hydroxyurea intolerant (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly.

therapy is a relapse of any myelofibrosis in a human subject following ruxolitnb or fedratinib therapy. In an embodiment, the BTK inhibitor is the compound selected from Table 1 and pharmaceutically acceptable salts thereof. In an embodiment, the human is suffering from splenomegaly, extramedullary hematopoiesis or fibrosis characterized by one or more mutations selected from the group consisting of JAK2V617F, MPL, CALR and combinations thereof.

In some embodiments, the BET inhibitor is administered once a day, two times per day, three times per day, four times per day, or five times per day. In some embodiments, the BTK inhibitor is administered at a dosage of about 40 mg/day to about 1000 mg/day. In some embodiments, the BTK inhibitor is administered orally. In some embodiments, the BTK inhibitor and the BET inhibitor are administered simultaneously, sequentially or intermittently. Doses and dosing for the BET inhibitor are as described herein.

In some embodiments, the invention encompasses pharmaceutical combinations comprising: (a) a BTK inhibitor; (b) a BET inhibitor; and (c) a pharmaceutically-acceptable excipient. In some embodiments, the combination provides a synergistic therapeutic effect compared to administration of the BTK inhibitor or the BET inhibitor alone. In some embodiments, the combination sensitizes myelofibrosis to the BTK inhibitor. In some embodiments, the BET inhibitor is a compound selected from Table 2 or a pharmaceutically acceptable salt thereof. In some embodiments, the BTK inhibitor is a compound selected from Table 1 or a pharmaceutically acceptable salt thereof. In some embodiments, the combination is in a combined dosage form. In some embodiments, the combination is in separate dosage forms.

In some embodiments, the invention encompasses use of a therapeutically effective amount of a combination comprising a BTK inhibitor and a BET inhibitor for treating splenomegaly, extramedullary hematopoiesis or fibrosis in a human subject in need thereof. In some embodiments, the combination provides a synergistic therapeutic effect compared to administration of the BTK inhibitor or the BET inhibitor alone. In some embodiments, the combination sensitizes a malignant CD34+ myeloid cell to the BTK inhibitor. In some embodiments, the BET inhibitor comprises a compound from Table 2 or a pharmaceutically acceptable salt thereof. In some embodiments, the splenomegaly, extramedullary hematopoiesis or fibrosis is associated with primary myelofibrosis, also known as chronic idiopathic myelofibrosis. This is in contrast with myelofibrosis that develops secondary to polycythemia vera or essential thrombocythaemia. In some embodiments, however, the invention encompasses treating splenomegaly, extramedullary hematopoiesis or fibrosis that develops secondary to polycythemia vera or essential thrombocythaemia. In an embodiment, the myelofibrosis is selected from the group consisting of primary myelofibrosis, secondary myelofibrosis, myelofibrosis secondary to polycythemia vera, myelofibrosis secondary to essential thrombocythemia, myelofibrosis secondary to chronic myeloid leukemia, and idiopathic myelofibrosis. In an embodiment, the myelofibrosis is selected from the group consisting of primary myelofibrosis, post-polycythemia vera myelofibrosis, and post-essential thrombocythemia myelofibrosis. In an embodiment, the primary myelofibrosis is selected from the group consisting of prefibrotic/early stage PMF and overt fibrotic stage PMF. In an embodiment, the human is determined as hydroxyurea intolerant (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly.

In an embodiment, the human subject is JAK2 inhibitor naïve (i.e. has never received therapy with a JAK2 inhibitor. In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any MPN in a human subject receiving ruxolitinib or fedratinib, or (ii) a relapse of any myelofibrosis in a human subject following ruxolitinb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib therapy is a relapse of any myelofibrosis in a human subject following ruxolitinb or fedratinib therapy. In an embodiment, the BTK inhibitor is the compound selected from Table 1 and pharmaceutically acceptable salts thereof.

In some embodiments, the invention encompasses use of a therapeutically effective amount of a combination comprising a BTK inhibitor and a BET inhibitor for treating myelofibrosis comprising administering to a human subject in need thereof a therapeutically effective amount of a combination comprising a BTK inhibitor and a BET inhibitor. In some embodiments, the combination provides a synergistic therapeutic effect compared to administration of the BTK inhibitor or the BET inhibitor alone. In some embodiments, the combination sensitizes the myelofibrosis to the BTK inhibitor. In some embodiments, the BET inhibitor is a compound selected from Table 2 or a pharmaceutically acceptable salt thereof. In some embodiments, the BTK inhibitor is a compound selected from Table 1 or a pharmaceutically acceptable salt thereof. In some embodiments, myelofibrosis is primary myelofibrosis, also known as chronic idiopathic myelofibrosis. This is in contrast with myelofibrosis that develops secondary to polycythemia vera or essential thrombocythaemia. In some embodiments, however, the invention encompasses treating splenomegaly due to myelofibrosis that develops secondary to polycythemia vera or essential thrombocythaemia. In some embodiments, the BTK inhibitor is a compound selected from Table 1 or a pharmaceutically acceptable salt thereof in combination with a compounds selected from Table 2 or a pharmaceutically acceptable salt thereof. In an embodiment, the human is determined as hydroxyurea intolerant (unacceptable side effects). In an embodiment, the human subject is determined as hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject is JAK2 inhibitor naïve (i.e. has never received therapy with a JAK2 inhibitor. In an embodiment, the human subject is JAK2 inhibitor intolerant. In an embodiment, the human subject is JAK2 inhibitor ineligible due to a low platelet count. In an embodiment, the human subject has relapsed after JAK2 inhibitor treatment. In an embodiment, the human subject is refractory to JAK2 inhibitor treatment. In an embodiment, the human subject failed ruxolitinib or fedratinib therapy. Failed ruxolitinib or fedratinib therapy includes, but is not limited to, (i) the absence of a reduction in the severity or progression of any MPN in a human subject receiving ruxolitinib or fedratinib, or (ii) a relapse of any myelofibrosis in a human subject following ruxolitinb or fedratinib therapy. In an embodiment, failed ruxolitinib or fedratinib therapy is the absence of a reduction in the severity or progression of any myelofibrosis in a human subject receiving ruxolitinib or fedratinib. In an embodiment, failed ruxolitinib or fedratinib therapy is a relapse of any myelofibrosis in a human subject following ruxolitinb or fedratinib therapy. In an embodiment, the BTK inhibitor is the compound selected from Table 1 and pharmaceutically acceptable salts thereof. In an embodiment, the human is suffering from splenomegaly, extramedullary hematopoiesis or fibrosis characterized by one or more mutations selected from the group consisting of JAK2V617F, MPL, CALR and combinations thereof.

Pharmaceutical Compositions

In some embodiments, the invention provides pharmaceutical compositions comprising a BTK inhibitor compound selected from Table 1 or a pharmaceutically acceptable salt thereof for myelofibrosis. In some embodiments, the invention provides pharmaceutical compositions comprising a BTK inhibitor compound selected from Table 1 or a pharmaceutically acceptable salt thereof for treating myelofibrosis, primary myelofibrosis, or idiopathic myelofibrosis. In an embodiment, the myelofibrosis is selected from primary myelofibrosis, post-polycythemia vera myelofibrosis, and post-essential thrombocythemia myelofibrosis.

In some embodiments, the invention provides pharmaceutical compositions comprising a BTK inhibitor compound selected from Table 1 or a pharmaceutically acceptable salt thereof for treating myeleofibrosis secondary to polycythemia vera, essential thrombocytothemia or chronic myeloid leukemia.

The pharmaceutical compositions are typically formulated to provide a therapeutically effective amount of a BTK inhibitor compound selected from Table 1 or a pharmaceutically acceptable salt thereof. Where desired, the pharmaceutical compositions contain a pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants. Where desired, other ingredients in addition to the BTK inhibitor or a pharmaceutically acceptable salt thereof may be mixed into a preparation or both components may be formulated into separate preparations for use in combination separately or at the same time.

In selected embodiments, the concentration of the BTK inhibitor or a pharmaceutically acceptable salt thereof provided in the pharmaceutical compositions of the invention is less than, for example, 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v or v/v.

In selected embodiments, the concentration of the BTK inhibitor or a pharmaceutically acceptable salt thereof provided in the pharmaceutical compositions of the invention is independently greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002% or 0.0001% w/w, w/v, or v/v.

In selected embodiments, the concentration of the BTK inhibitor or a pharmaceutically acceptable salt thereof is independently in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12% or approximately 1% to approximately 10% w/w, w/v or v/v.

In selected embodiments, the concentration of the BTK inhibitor or a pharmaceutically acceptable salt thereof is independently in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In selected embodiments, the amount of the BTK inhibitor or a pharmaceutically acceptable salt thereof is independently equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g or 0.0001 g.

In selected embodiments, the amount of the BTK inhibitor or a pharmaceutically acceptable salt thereof is independently more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g or 10 g.

The BTK inhibitor compounds in Table 1 and pharmaceutically acceptable salts thereof are effective over a wide dosage range. For example, in the treatment of adult humans, dosages independently ranging from 0.01 to 1000 mg, from 0.5 to 100 mg, from 1 to 50 mg per day, and from 5 to 40 mg per day are examples of dosages that may be used. The exact dosage will depend upon the route of administration, the form in which the compound is administered, the gender and age of the subject to be treated, the body weight of the subject to be treated, and the preference and experience of the attending physician.

Described below are non-limiting exemplary pharmaceutical compositions and methods for preparing the same.

Pharmaceutical Compositions for Oral Administration

In selected embodiments, the invention provides a pharmaceutical composition for oral administration comprising a BTK inhibitor compound selected from Table 1 or a pharmaceutically acceptable salt thereof, and a pharmaceutical excipient suitable for oral administration.

In selected embodiments, the invention provides a solid pharmaceutical composition for oral administration containing: (i) an effective amount of the BTK inhibitor or a pharmaceutically acceptable salt thereof, in combination and (ii) a pharmaceutical excipient suitable for oral administration. In selected embodiments, the composition further contains (iii) an effective amount of at least one additional active ingredient.

In selected embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods, but all methods include the step of bringing the active ingredient(s) into association with the carrier, which constitutes one or more necessary ingredients. In general, the compositions are prepared by uniformly and intimately admixing the active ingredient(s) with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The invention further encompasses anhydrous pharmaceutical compositions and dosage forms since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

The BTK inhibitor or a pharmaceutically acceptable salt thereof can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which disintegrate in the bottle. Too little may be insufficient for disintegration to occur, thus altering the rate and extent of release of the active ingredients from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In an embodiment, the composition may include a solubilizer to ensure good solubilization and/or dissolution of the compound of the present invention and to minimize precipitation of the compound of the present invention. This can be especially important for compositions for non-oral use, such as for compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, epsilon-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethyl pyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a patient using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer may also be used, such as 5%, 2%, 1% or even less. Typically, the solubilizer may be present in an amount of about 1% to about 100%, more typically about 5% to about 25% by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals and alkaline earth metals. Examples may include, but are not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid and uric acid.

Pharmaceutical Compositions for Injection

In selected embodiments, the invention provides a pharmaceutical composition for injection comprising a BTK inhibitor compound selected from Table 1 or a pharmaceutically acceptable salt thereof, and a pharmaceutical excipient suitable for injection. Components and amounts of agents in the compositions are as described herein.

The forms in which the compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol and liquid polyethylene glycol (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid and thimerosal.

Sterile injectable solutions are prepared by incorporating the BTK inhibitor or a pharmaceutically acceptable salt thereof in the required amounts in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Administration of the BTK inhibitor or a pharmaceutically acceptable salt thereof or pharmaceutical composition of these compounds can be effected by any method that enables delivery of the compounds to the site of action. These methods include oral routes, intraduodenal routes, parenteral injection (including intravenous, intra-arterial, subcutaneous, intramuscular, intravascular, intraperitoneal or infusion), topical (e.g., transdermal application), rectal administration, via local delivery by catheter or stent or through inhalation. The combination of compounds can also be administered intraadiposally or intrathecally.

Exemplary parenteral administration forms include solutions or suspensions of active compound in sterile aqueous solutions, for example, aqueous propylene glycol or dextrose solutions. Such dosage forms can be suitably buffered, if desired.

The invention also provides kits. The kits include a BTK inhibitor compound selected from Table 1 or a pharmaceutically acceptable salt thereof, either alone or in combination in suitable packaging, and written material that can include instructions for use, discussion of clinical studies and listing of side effects. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. The kit may further contain another active pharmaceutical ingredient. Suitable packaging and additional articles for use (e.g., measuring cup for liquid preparations, foil wrapping to minimize exposure to air, and the like) are known in the art and may be included in the kit. Kits described herein can be provided, marketed and/or promoted to health providers, including physicians, nurses, pharmacists, formulary officials, and the like. Kits may also, in selected embodiments, be marketed directly to the consumer. In an embodiment, the invention provides a kit comprising the BTK inhibitor or a pharmaceutically acceptable salt thereof for use in the treatment of myelofibrosis as described herein.

Dosages and Dosing Regimens

The amount of a BTK inhibitor or a pharmaceutically acceptable salt thereof administered will be dependent on the human being treated, the severity of the disorder or condition, the rate of administration, the disposition of the compounds and the discretion of the prescribing physician. However, an effective dosage is in the range of about 0.001 to about 100 mg per kg body weight per day, such as about 1 to about 35 mg/kg/day, in single or divided doses. For a 70 kg human, this would amount to about 0.05 to 7 g/day, such as about 0.05 to about 2.5 g/day. In some instances, dosage levels below the lower limit of the aforesaid range may be more than adequate, while in other cases still larger doses may be employed without causing any harmful side effect—e.g., by dividing such larger doses into several small doses for administration throughout the day.

In some embodiments, a BTK inhibitor or a pharmaceutically acceptable salt thereof is administered in a single dose. Mutiple daily doses are also empbodied, for example, twice daily. Typically, such administration will be oral. However, other routes may be used as appropriate.

In some embodiments, a BTK inhibitor or a pharmaceutically acceptable salt thereof is administered in multiple doses for treating myelofibrosis. In an embodiment, a BTK inhibitor or a pharmaceutically acceptable salt thereof is administered in multiple doses. In an embodiment, dosing may be once, twice, three times, or four times per day. In an embodiment, dosing may be selected from the group consisting of once a day, twice a day, three times a day, or four times a day, once every other day, once weekly, twice weekly, three times weekly, four times weekly, biweekly, and monthly. In other embodiments, a BTK inhibitor or a pharmaceutically acceptable salt thereof is administered about once per day to about four times per day. In some embodiments a BTK inhibitor or a pharmaceutically acceptable salt thereof is administered once daily, while in other embodiments a BTK inhibitor or a pharmaceutically acceptable salt thereof is administered twice daily, and in other embodiments a BTK inhibitor or a pharmaceutically acceptable salt thereof is administered three times daily. In some embodiments a BTK inhibitor or a pharmaceutically acceptable salt thereof is administered three times a week, including every Monday, Wednesday, and Friday.

Administration of a BTK inhibitor or a pharmaceutically acceptable salts thereof may continue as long as necessary. In some embodiments, a BTK inhibitor or a pharmaceutically acceptable salt thereof is administered for more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or more days. In some embodiments, a BTK inhibitor or a pharmaceutically acceptable salt thereof is administered for less than 28, 14, 7, 6, 5, 4, 3, 2, or 1 day. In some embodiments, a BTK inhibitor or a pharmaceutically acceptable salt thereof is administered for about 14 days, about 21 days, about 28 days, about 35 days, about 42 days, about 49 days, or about 56 days. In some embodiments, a BTK inhibitor or a pharmaceutically acceptable salt thereof is administered chronically on an ongoing basis—e.g., for the treatment of chronic effects. In another embodiment the administration of a BTK inhibitor or a pharmaceutically acceptable salt thereof continues for less than about 7 days. In yet another embodiment the administration continues for more than about 6, 10, 14, 28 days, two months, three months, four months, five months, six months, seven months, eight months, nine months, ten months, eleven months or one year. In some embodiments, the administration continues for more than about one year, two years, three years, four years, or five years. In some embodiments, continuous dosing is achieved and maintained as long as necessary.

In some embodiments, an effective dosage of a BTK inhibitor or a pharmaceutically acceptable salt thereof is in the range of about 1 mg to about 600 mg, about 10 mg to about 500 mg, about 20 mg to about 450 mg, about 25 mg to about 200 mg, about 10 mg to about 200 mg, about 20 mg to about 150 mg, about 30 mg to about 120 mg, about 10 mg to about 90 mg, about 20 mg to about 80 mg, about 30 mg to about 70 mg, about 40 mg to about 60 mg, about 45 mg to about 55 mg, about 48 mg to about 52 mg, about 50 mg to about 150 mg, about 60 mg to about 140 mg, about 70 mg to about 130 mg, about 80 mg to about 120 mg, about 90 mg to about 110 mg, about 95 mg to about 105 mg, about 150 mg to about 250 mg, about 160 mg to about 240 mg, about 170 mg to about 230 mg, about 180 mg to about 220 mg, about 190 mg to about 210 mg, about 195 mg to about 205 mg, or about 198 to about 202 mg. In some embodiments, an effective dosage of a BTK inhibitor or a pharmaceutically acceptable salt thereof is about 15 mg, about 25 mg, about 30 mg, about 50 mg, about 50 mg, about 75 mg, about 90 mg, about 100 mg, about 120 mg, about 125 mg, about 150 mg, about 175 mg, about 180 mg, about 200 mg, about 225 mg, about 240 mg, about 250 mg, about 275 mg, about 300 mg, about 325 mg, about 350 mg, about 360 mg, about 375 mg, about 400 mg, about 425 mg, about 450 mg, about 475 mg, about 480 mg, or about 500 mg. In some embodiments, an effective dosage of a BTK inhibitor or a pharmaceutically acceptable salt thereof is 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg.

In some embodiments, an effective dosage of a BTK inhibitor or a pharmaceutically acceptable salt thereof is in the range of about 0.01 mg/kg to about 4.3 mg/kg, about 0.15 mg/kg to about 3.6 mg/kg, about 0.3 mg/kg to about 3.2 mg/kg, about 0.35 mg/kg to about 2.85 mg/kg, about 0.15 mg/kg to about 2.85 mg/kg, about 0.3 mg to about 2.15 mg/kg, about 0.45 mg/kg to about 1.7 mg/kg, about 0.15 mg/kg to about 1.3 mg/kg, about 0.3 mg/kg to about 1.15 mg/kg, about 0.45 mg/kg to about 1 mg/kg, about 0.55 mg/kg to about 0.85 mg/kg, about 0.65 mg/kg to about 0.8 mg/kg, about 0.7 mg/kg to about 0.75 mg/kg, about 0.7 mg/kg to about 2.15 mg/kg, about 0.85 mg/kg to about 2 mg/kg, about 1 mg/kg to about 1.85 mg/kg, about 1.15 mg/kg to about 1.7 mg/kg, about 1.3 mg/kg mg to about 1.6 mg/kg, about 1.35 mg/kg to about 1.5 mg/kg, about 2.15 mg/kg to about 3.6 mg/kg, about 2.3 mg/kg to about 3.4 mg/kg, about 2.4 mg/kg to about 3.3 mg/kg, about 2.6 mg/kg to about 3.15 mg/kg, about 2.7 mg/kg to about 3 mg/kg, about 2.8 mg/kg to about 3 mg/kg, or about 2.85 mg/kg to about 2.95 mg/kg. In some embodiments, an effective dosage of a BTK inhibitor or a pharmaceutically acceptable salt thereof is about 0.35 mg/kg, about 0.7 mg/kg, about 1 mg/kg, about 1.4 mg/kg, about 1.8 mg/kg, about 2.1 mg/kg, about 2.5 mg/kg, about 2.85 mg/kg, about 3.2 mg/kg, or about 3.6 mg/kg.

In some embodiments, a BTK inhibitor or a pharmaceutically acceptable salt thereof is administered at a dosage of 10 to 500 mg BID, including a dosage of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg BID.

In some embodiments, a BTK inhibitor or a pharmaceutically acceptable salt thereof is administered at a dosage of 10 to 600 mg QD, including a dosage of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, and 480 mg QD.

An effective amount of a BTK inhibitor or a pharmaceutically acceptable salt thereof may be administered in either single or multiple doses by any of the accepted modes of administration of agents having similar utilities, including buccal, sublingual, and transdermal routes, by intra-arterial injection, intravenously, parenterally, intramuscularly, subcutaneously or orally.

In some embodiments, a BTK inhibitor or a pharmaceutically acceptable salt thereof is administered to a subject intermittently, known as intermittent administration. By "intermittent administration" it is meant a period of administration of a therapeutically effective dose of a BTK inhibitor or a pharmaceutically acceptable salt thereof, followed by a time period of discontinuance, which is then followed by another administration period and so on. In each administration period, the dosing frequency can be independently select from three times daily, twice daily, daily, once weekly, twice weekly, three times weekly, four times weekly, five times weekly, six times weekly or monthly. In an embodiment, the BTK inhibitor is a compound selected from Table 1 or a pharmaceutically acceptable salt thereof.

By "period of discontinuance" or "discontinuance period" or "rest period", it is meant to the length of time when discontinuing of the administration of a BTK inhibitor or a pharmaceutically acceptable salt thereof. The time period of discontinuance may be longer or shorter than the administration period or the same as the administration period. During the discontinuance period, other therapeutic agents other than a BTK inhibitor or a pharmaceutically acceptable salt thereof may be administered. The discontinuance period may be necessary to alleviate any toxic effects associated with a particular BTK inhibitor compound.

In an embodiment, a BTK inhibitor or a pharmaceutically acceptable salt thereof is administered to a human subject in need thereof for treating myelofibrosis for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, elven weeks, three months, thirteen weeks, fourteen weeks, fifteen weeks, four months, and more days, in which a BTK inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject weekly; and the discontinuance period is about two weeks. In an embodiment, the first administration period and the second administration period are about four weeks, in which a BTK inhibitor or a pharmaceutically acceptable salt thereof is administered to a subject daily; and the discontinuance period is about two weeks. In an embodiment, the first administration period and the second administration period are about four weeks, in which a BTK inhibitor or a pharmaceutically acceptable salt thereof is administered to a subject weekly; and the discontinuance period is about two weeks. In an embodiment, the BTK inhibitor is a compound selected from Table 1 or a pharmaceutically acceptable salt thereof.

In an embodiment, a BTK inhibitor or a pharmaceutically acceptable salt thereof is administered to a human subject in need thereof for treating myelofibrosis secondary to polycythemia vera for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, elven weeks, three months, thirteen weeks, fourteen weeks, fifteen weeks, four months, and more days, in which a BTK inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject weekly; and the discontinuance period is about two weeks. In an embodiment, the first administration period and the second administration period are about four weeks, in which a BTK inhibitor or a pharmaceutically acceptable salt thereof is administered to a subject daily; and the discontinuance period is about two weeks. In an embodiment, the first administration period and the second administration period are about four weeks, in which a BTK inhibitor or a pharmaceutically acceptable salt thereof is administered to a subject weekly; and the discontinuance period is about two weeks. In an embodiment, the BTK inhibitor is the compound of selected from Table 1 and pharmaceutically acceptable salts thereof.

In an embodiment, a BTK inhibitor or a pharmaceutically acceptable salt thereof is administered to a human subject in need thereof for treating myelofibrosis secondary to essential thrombocythemia for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, elven weeks, three months, thirteen weeks, fourteen weeks, fifteen weeks, four months, and more days, in which a BTK inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject weekly; and the discontinuance period is about two weeks. In an embodiment, the first administration period and the second administration period are about four weeks, in which a BTK inhibitor or a pharmaceutically acceptable salt thereof is administered to a subject daily; and the discontinuance period is about two weeks. In an embodiment, the first administration period and the second administration period are about four weeks, in which a BTK inhibitor or a pharmaceutically acceptable salt thereof is administered to a subject weekly; and the discontinuance period is about two weeks. In an embodiment, the BTK inhibitor is a compound selected from Table 1 or a pharmaceutically acceptable salt thereof.

In an embodiment, a BTK inhibitor or a pharmaceutically acceptable salt thereof is administered to a human subject in need thereof for treating myelofibrosis secondary to chronic myeloid leukemia for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, elven weeks, three months, thirteen weeks, fourteen weeks, fifteen weeks, four months, and more days, in which a BTK inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject weekly; and the discontinuance period is about two weeks. In an embodiment, the first administration period and the second administration period are about four weeks, in which a BTK inhibitor or a pharmaceutically acceptable salt thereof is administered to a subject daily; and the discontinuance period is about two weeks. In an embodiment, the first administration period and the second administration period are about four weeks, in which a BTK inhibitor or a pharmaceutically acceptable salt thereof is administered to a subject weekly; and the discontinuance period is about two weeks. In an embodiment, the BTK inhibitor is a compound selected from Table 1 or a pharmaceutically acceptable salt thereof.

In an embodiment, a BTK inhibitor or a pharmaceutically acceptable salt thereof is administered to a human subject in need thereof for treating primary myelofibrosis for a first administration period, then followed by a discontinuance period, then followed by a second administration period, and so on. The first administration period, the second administration period, and the discontinuance period are independently selected from the group consisting of more than 1, 2, 3, 4, 5, 6, 7, 8, 9, 10, 11, 12, 13, 14, 15, 16, 17, 18, 19, 20, 21, 22, 23, 24, 25, 26, 27, 28, 29, one month, five weeks, six weeks, seven weeks, two months, nine weeks, ten weeks, elven weeks, three months, thirteen weeks, fourteen weeks, fifteen weeks, four months, and more days, in which a BTK inhibitor or a pharmaceutically acceptable salt thereof is administered to a subject three times daily, twice daily, daily, once weekly, twice weekly, three times weekly, four times weekly, five times weekly, six times weekly or monthly. In an embodiment, the first administration period is at same length as the second administration period. In an embodiment, the first administration period is shorter than the second administration period. In an embodiment, the first administration period is longer than the second administration period. In an embodiment, the first administration period and the second administration period are about one week, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject daily; and the discontinuance period is about two weeks. In an embodiment, the first administration period and the second administration period are about three weeks, in which a BTK inhibitor or a pharmaceutically acceptable salt thereof is administered to a subject weekly; and the discontinuance period is about two weeks. In an embodiment, the first administration period and the second administration period are about four weeks, in which a BTK inhibitor or a pharmaceutically acceptable salt thereof is administered to a subject daily; and the discontinuance period is about two weeks. In an embodiment, the first administration period and the second administration period are about four weeks, in which a BTK inhibitor or a pharmaceutically acceptable salt thereof is administered to a subject weekly; and the discontinuance period is about two weeks. In an embodiment, the BTK inhibitor is a compound selected from Table 1 or a pharmaceutically acceptable salt thereof.

In an embodiment, a BTK inhibitor or a pharmaceutically acceptable salt thereof is administered to a subject in need thereof for treating myelofibrosis for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the BTK inhibitor is selected from any of the compounds in Table 1 or a pharmaceutically acceptable salt thereof. In an embodiment, the BTK inhibitor is orally administered at a dose of 100 mg twice a day.

In an embodiment, a BTK inhibitor or a pharmaceutically acceptable salt thereof is administered to a subject in need thereof for treating primary myelofibrosis for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the BTK inhibitor is selected from any of the compounds in Table 1 or pharmaceutically acceptable salts thereof. In an embodiment, the human subject is hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject failed ruxolitinib or fedratinib therapy.

In an embodiment, a BTK inhibitor or a pharmaceutically acceptable salt thereof is administered to a subject in need thereof for treating myelofibrosis secondary to polycythemia vera for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the BTK inhibitor compound is selected from Table 1 and pharmaceutically acceptable salts thereof.

In an embodiment, a BTK inhibitor or a pharmaceutically acceptable salt thereof is administered to a subject in need thereof for treating myelofibrosis secondary to essential thrombocythemia for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the BTK inhibitor compound is selected from Table 1 and pharmaceutically acceptable salts thereof.

In an embodiment, a BTK inhibitor or a pharmaceutically acceptable salt thereof is administered to a subject in need thereof for treating myelofibrosis secondary to chronic myeloid leukemia for a period selected from 3 weeks, 6 weeks, 9 weeks, 12 weeks, 15 weeks, 18 weeks, 21 weeks, 24 weeks, 27 weeks, 30 weeks, 33 weeks, 36 weeks, 39 weeks, 42 weeks, 45 weeks, 48 weeks, 51 weeks, 54 weeks, 57 weeks, 60 weeks, 63 weeks, 66 weeks, 69 weeks, 72 weeks, 75 weeks, 78 weeks, 81 weeks, 84 weeks, 87 weeks, 90 weeks, 93 weeks, 96 weeks, 99 weeks, 102 weeks, 105 weeks, 108 weeks, 111 weeks, 114 weeks, 117 weeks, 120 weeks, 123 weeks, 126 weeks, 129 weeks, 132 weeks, 135 weeks, 138 weeks, 141 weeks, 144 weeks, 147 weeks, 150 weeks, 153 weeks, and 156 weeks, wherein the BTK inhibitor compound is selected from Table 1 and pharmaceutically acceptable salts thereof.

In some embodiments, the human subject is hydroxyurea resistant (inadequate response). In an embodiment, the human subject has splenomegaly. In an embodiment, the human subject has splenomegaly and is phlebotomy-dependent. In an embodiment, the human subject is phlebotomy-dependent without splenomegaly. In an embodiment, the human subject failed ruxolitinib or fedratinib therapy.

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.

Example 1: BTK Inhibitor Monotherapy for Patients with Myeleofibrosis

The purpose of this study is to investigate the safety and efficacy of a BTK inhibitor compound in patients with myeleofibrosis. Thirty MF patients will be enrolled in the study and will be administered a BTK inhibitor compound 200 or 300 mg once daily. The inclusion criteria are (1) previously non-treated with at least one other agent (hydroxyurea, interferon, anagrelide), (2) ≥18 years of age, (3) acceptable pre-study organ function during screening as defined as: Total bilirubin ≤1.5 times the upper limit of normal (ULN) unless due to Gilbert's disease or hemolysis, Aspartate aminotransferase (AST) and alanine aminotransferase (ALT) ≤2.5 times ULN, Serum creatinine ≤1.5×ULN, and (3) women of childbearing age and males must agree to use adequate contraception (i.e., hormonal or barrier method of birth control; abstinence) prior to study entry and for the duration of study participation. Should a female subject become pregnant or suspect she is pregnant while participating in this study, she should be excluded from the study immediately During or at the end of the study, each MF patient will be evaluated by the following items to determine the safety and efficacy of the BTK inhibitor compound (1) hematologic response; (2) JAK2V617F allele burden reduction; (3) changes in bone marrow histopathologic abnormalities; (4) reduction in baseline reticulin/collagen fibrosis; (5) incidence of venous and arterial thrombosis; and (5) changes in MF related symptoms.

Example 2: An Open-Label, Phase 2a/2b Study of a BTK Inhibitor Compound

There is a significant unmet need for improved therapies in patients with myelofibrosis who have primary resistance to, suboptimal responses to, or who have relapsed after treatment with ruxolitinib. BTK inhibitor compounds are an orally bioavailable, small molecule, cytotoxic chemotherapeutic agent that binds to BTK.

Study Design

This is an open-label, 2-part (Part A and Part B), Phase 2a/2b study of the compound of Formula (I) in subjects with PMF, post PV-MF, or post ET-MF who have failed ruxolitinib therapy. Approximately 190 subjects will be enrolled in the study (90 in Part A and 100 in Part B).

Part A (N=90): In Part A of the study, subjects will be randomly assigned to 1 of 3 treatment groups: Cohort 1, N=30 subjects: The BTK inhibitor compound at 280 mg once daily. Cohort 2, N=30 subjects: The BTK inhibitor compound at 420 mg once daily. Cohort 3, N=30 subjects: The BTK inhibitor compound at 560 mg once daily.

Part B (N=100): Approximately 100 subjects will be enrolled into Part B and treated at the recommended dose and schedule from Part A. A Data Monitoring Committee (DMC) will convene every 3 months for Part A and Part B during the conduct of the study to review the safety data for the clinical study. The DMC will also convene after all subjects in Part A have had the opportunity to complete the Week 24 assessment. The DMC will determine the recommended dose and schedule of the BTK inhibitor compound based on the efficacy and safety data from Part A. In Part A and Part B, subjects will receive the BTK inhibitor compound orally (PO) once daily on a 28-day cycle. Dose reductions for hematologic and nonhematologic toxicity will be allowed. All subjects should be treated until disease progression or lack of tolerability. The definition of disease progression is based on imaging and modified ELN criteria: increase in splenic volume of ≥25% from on-study nadir by MRI (or CT) by central imaging review, leukemic transformation confirmed by a bone marrow blast count of ≥20% or a peripheral blood blast content of ≥20% associated with an absolute blast count of ≥1×10$^9$/L that lasts for at least 2 weeks.

Study Objectives

| Primary Objectives | Endpoint/Outcome Measure |
|---|---|
| To determine spleen response | The proportion of subjects achieving a >35% spleen volume reduction from Baseline to Week 24, as assessed by magnetic resonance imaging (MRI) or computed tomography (CT) scan |

Inclusion Criteria

Subjects in both Part A and Part B must meet all of the following criteria in order to be eligible for the study: 1. Adults >18 years of age, 2. Palpable splenomegaly at least 5 cm below left costal margin, 3. Confirmed diagnosis of PMF, post-V-MF, or post-ET-MF, as assessed by treating physician according to the World Health Organization (WHO) criteria, 4. High-risk, intermediate-2 risk, or intermediate-1 risk, defined by Dynamic International Prognostic System (DIPSS), 5. ECOG performance status of 0 to 2, 6. Adequate hematological, hepatic, and renal organ function (as per protocol definition and within 14 days prior to the first dose of the BTK inhibitor compound), Hematologic: ANC ≥1.0×10$^9$/L in the absence of growth factors during the prior 7 days; platelet count ≥100×10$^9$/L; Peripheral blood blast count <10%. Hepatic: total bilirubin ≤2.0 times the upper limit of normal (ULN), unless Gilbert's Syndrome; aspartate transaminase/serum glutamic oxaloacetic transaminase (AST/SGOT) and alanine transaminase/serum glutamic pyruvic transaminase (ALT/SGPT) ≤2.5 ULN•Renal: estimated creatinine clearance >45 mL/min by Cockcroft Gault:

$$eC_{Cr} = \frac{(140 - \text{Age}) \times \text{Mass (in kilograms)} \times [0.85 \text{ if Female}]}{72 \times \text{Serum Creatinine (in mg/dL)}}.$$

7. Females of childbearing potential and males who have partners of childbearing potential must agree to use an effective contraception method during the study. In addition, males must continue to use contraception for 3 months after the last dose of study drug and females must continue to use contraception for 1 week after the last dose of study drug. Effective birth control includes (a) combined, estrogen and progestogen containing, hormonal contraception (oral, intravaginal, transdermal); (b) progestogen-only hormonal contraception (oral, injectable, implantable); (c) intrauterine device; (d) intrauterine hormonereleasing system; (e) bilateral tubal occlusion; (f) vasectomised partner; and (g) sexual abstinence.

Subjects in Part A must meet the following ruxolitinib treatment failure criteria in order to be eligible for the study: Ruxolitinib treatment failure in Part A must meet either criterion (a) or (b) below: (a) Either a lack of spleen response defined as receiving at least 12 weeks of ruxolitinib treatment and having both of the following: persistent splenomegaly, by physical exam, that is palpable ≥5 cm below the lower costal margin (LCM), and TSS of >10 on the MPN-SAF TSS 2.0 or patients with a single symptom score of >5 or two symptoms of >3, including only the symptoms of left upper quadrant pain, bone pain, itching, or night sweats. (b) or progressive disease any time while on ruxolitinib treatment as defined by any one of the following: spleen volume increase by ≥25% from the nadir as assessed by MRI or CT, appearance of new splenomegaly that is palpable at least 5 cm below the LCM, a ≥100% increase in palpable distance, below the LCM, for baseline splenomegaly of 5 to 10 cm, a ≥50% increase in palpable distance, below the LCM, for baseline splenomegaly of >10 cm.

Subjects in Part B must meet the following ruxolitinib treatment failure criteria in order to be eligible for the study: Ruxolitinib treatment failure in Part B must meet either criterion (a) or (b) below: (a) Either a lack of spleen response defined as receiving at least 12 weeks of ruxolitinib treatment and having at least one of the following: for subjects that have a MRI or CT to assess ruxolitinib treatment, failure to have a least ≥35% reduction in spleen volume, a Baseline splenomegaly prior to ruxolitinib treatment that is palpable at 5 to 10 cm, below the LCM, but remains palpable, a Baseline splenomegaly prior to ruxolitinib treatment that is palpable >10 cm, below the LCM, but does not decrease by at least 50%, a baseline splenomegaly prior to ruxolitinib treatment that is palpable <5 cm, below the LCM, is not eligible to be considered as a ruxolitinib treatment failure; (b) or progressive disease any time while on ruxolitinib treatment as defined by any one of the following: spleen volume increase by ≥25% from the nadir as assessed by MRI or CT, appearance of new splenomegaly that is palpable at least 5 cm below the LCM, ≥100% increase in palpable distance, below the LCM, for baseline splenomegaly of 5 to 10 cm, ≥50% increase in palpable distance, below the LCM, for baseline splenomegaly of >10 cm.

Exclusion Criteria

Subjects in both Part A and Part B who meet any of the following criteria will not be eligible for the study: 1. Participation in another interventional clinical trial within the past 4 weeks of the first dose of the compound of Formula (I) (participation in observational studies is permitted). 2. Recent/concurrent treatment such as a major surgery, chemotherapy, immunomodulating therapy, biologic therapy, radiation therapy, or investigational therapy within 4 weeks or approximately 5 half lives of the first dose of the compound of Formula (I). 3. Prior splenectomy. 4. Splenic irradiation within 3 months prior to the first dose of the compound of Formula (I). 5. Prior allogeneic stem-cell transplantation or eligible for allogeneic stem cell transplantation. 6. Prior treatment with histone deacetylase (HDAC) inhibitors or BCL-2 inhibitors. 7. Prior BTK inhibitor therapy. 8. Women who are pregnant or breastfeeding. 9. History of major organ transplant. 10. Uncontrolled intercurrent illness including, but not limited to, acute hepatitis A; known history of human immunodeficiency virus (HIV)-positive; clinically significant cardiac disease (New York Heart Association Class III or IV); symptomatic congestive heart failure; unstable angina pectoris ventricular arrhythmia; or psychiatric illness/social situations that would limit compliance with study requirements. 11. Subjects with clinically significant bacterial, fungal, parasitic, or viral infection that requires therapy. Subjects with acute bacterial infections requiring antibiotic use should delay screening/enrollment until the course of antibiotic therapy has been completed. Other malignancy within the last 3 years, other than curatively treated basal cell or squamous cell skin cancer, carcinoma in situ of the cervix, organconfined or treated nonmetastatic prostate cancer with normal prostate-specific antigen, in situ breast carcinoma after complete surgical resection, or superficial transitional cell bladder carcinoma. 13. Grade 2 or higher QTc prolongation (>480 milliseconds per NCI-CTCAE criteria, version 5.0). 14. Hematopoietic growth factors (i.e., erythropoietin (Epo), granulocyte colony stimulating factor (GCSF), romiplostim) within 28 days prior to receiving the first dose of the compound of Formula (I). 15. Active or chronic bleeding within 4 weeks prior to the first dose of the compound of Formula (I).

Randomization Procedure

Part A: Subjects will be randomized in a 1:1:1 allocation scheme to one of three treatment cohorts. A contract clinical service provider will develop the Part A randomization schedule and the actual randomization assignment will be made through a secure Interactive Response Technology (IRT) system. Part B: Subjects will be randomized to the the BTK inhibitor compound dose and schedule recommended by the DMC.

Statistical Analysis

The DMC will convene every 3 months for Part A and Part B during the conduct of the study to review the safety data for the clinical study. The DMC will also convene after all subjects in Part A have had the opportunity to complete the Week 24 assessment. The DMC will determine the recommended dose and schedule of the BTK inhibitor compound for Part B based on the efficacy and safety data from Part A. Results of statistical analyses, descriptive summary statistics, and supportive listings will be presented by study part (A or B) and within Part A (by cohorts).

Study Duration

The study will be considered complete 2 years after the last subject is enrolled, at which time subjects who remain on study treatment will be evaluated for eligibility to enroll in a rollover study.

Example 3: BTK Inhibition in Healthy B-Cells and Myeloid Cells

Inhibition of BTK phosphorylation (activation) by Compound No. 128 (1-(4-(((6-amino-5-(4-phenoxyphenyl)pyrimidin-4-yl)amino)methyl)-4-fluoropiperidin-1-yl)prop-2-en-1-one) was assessed in healthy B-cells and in myeloid cell lines MOLM-13 basal and Hel-92 basal. Compound No. 128 was incubated with the myeloid cells lines for two hours with no stimulation and with healthy PBMC5 for two hours with 10 minutes of αIgM and $H_2O_2$ stimulation. As shown in Table 3, the potency of Compound No. 128 in myeloid cells is similar to its potency in healthy B-cells.

TABLE 3

| BTK Inhibition | |
|---|---|
| Cells | EC50 (nm) |
| Healthy B-cells | 16.9 |
| MOLM-13 basal | 21.4 |
| Hel-92 basal | 19.7 |

Example 4: Inhibition of Cell Migration Towards SDF-1 (CXCL12)

Figure 1B:
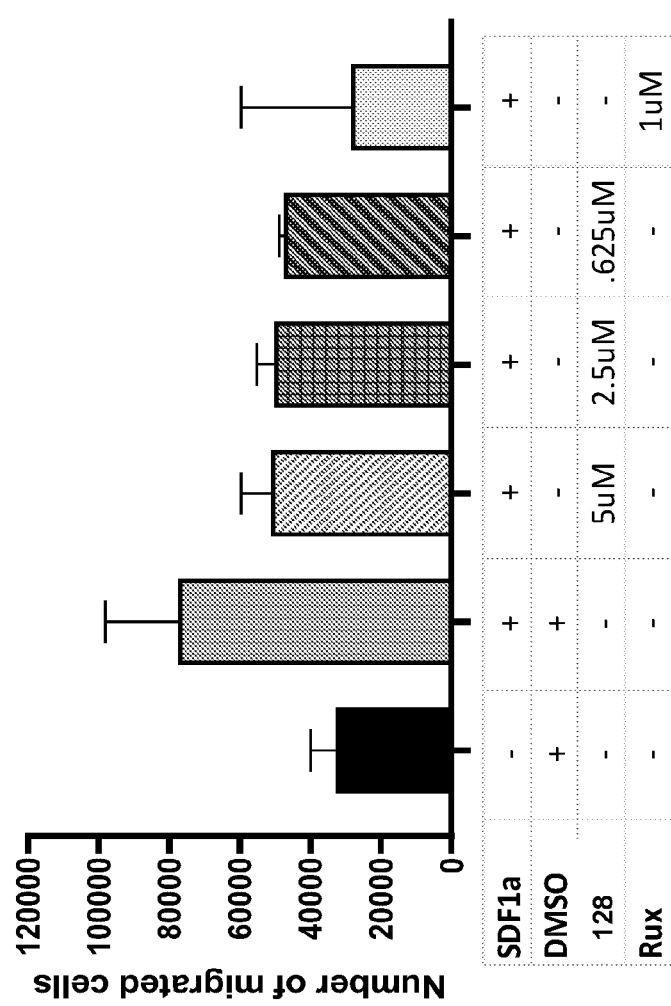

In MF, the spleen has high levels of SDF-1 compared to the blood. As a chemoattractant chemokine, SDF-1 draws cells along a concentration gradient. In vitro inhibition of cell migration through a permeable membrane by Compound No. 128 and ruxolitinib (Rux) was assessed using Hel-92 (V617F mut) cells. As shown in FIG. 1A and 1B, Compound No. 128 and ruxolitinib both inhibit cell migration towards SDF-1.

Example 5: Fibronectin Release

Figure 2:
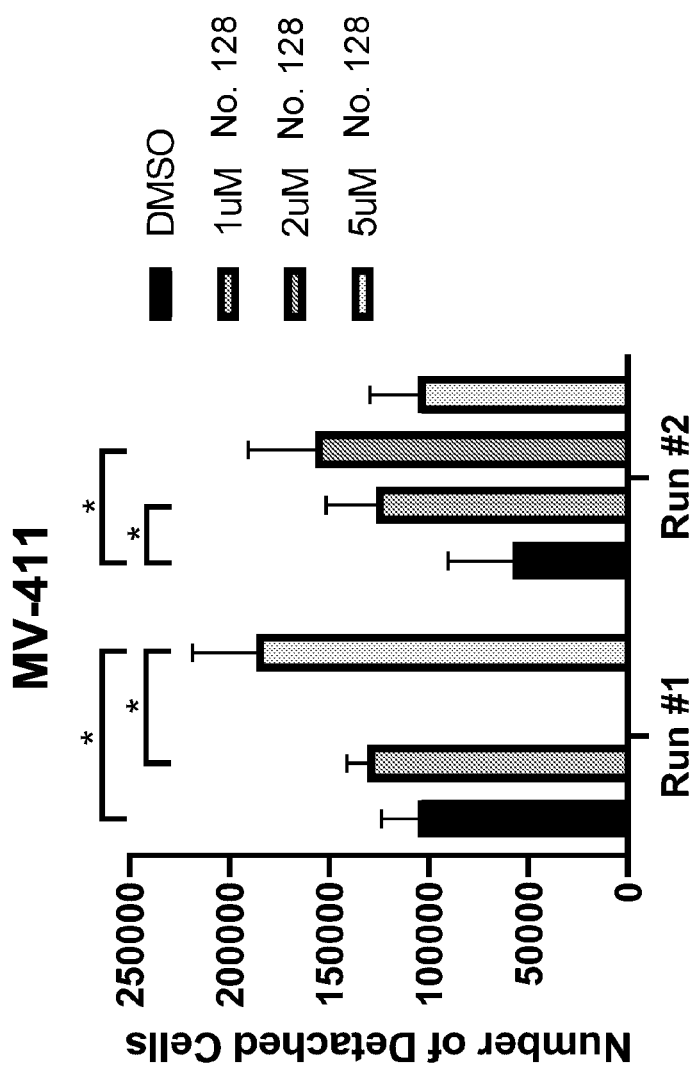
FIG. 2 is a graph showing release of cells from fibronectin.

Fibronectin is an important component of the microenvironment extracellular matrix and attaches to cells through VLA-4 (integrin α4β1). Detachment of cells from fibronectin after exposure to Compound No. 128 was assessed by plating $1 \times 10^6$ MV-411 cells on fibronectin-coated plates (3 replicates). The cells were allowed to adhere overnight at 37° C. and then unadhered cells were washed away. Next, attached cells were treated with DMSO or Compound No. 128 (1, 2, or 5 µm) for two hours at 37° C. Detached cells were then collected and cell numbers determined using CellTiter Glo. As shown in FIG. 2, cells detached from fibronectin after exposure to Compound No. 128.

Example 6: Expression of Surface Molecules Involved in Cell Adhesion

Figure 3:
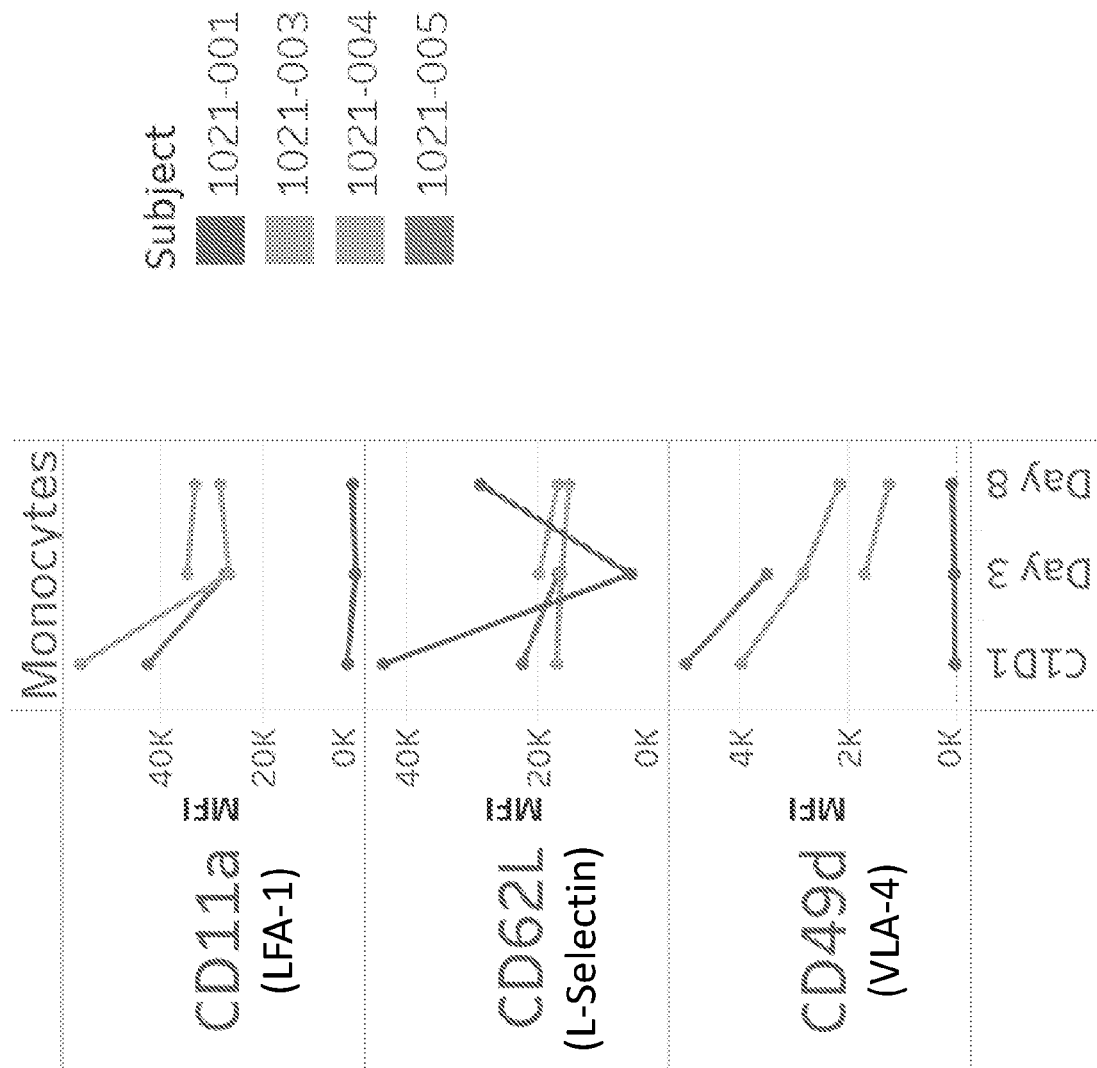
FIG. 3 is a graph showing levels of cell surface molecules.

A reduction in the expression of surface molecules involved in the adhesion of cells to their microenvironment may inhibit protection of malignant cells in various compartments. Monocytes from blood of COVID-19 patient treated with Compound No. 128 were assessed for levels of the surface molecules CD11a (LFA-1), CD62L (L-selectin), and CD49d (VLA-4). As shown in FIG. 3, treatment with Compound No. 128 reduced levels of surface molecules in some patients.

Example 7: Cytokine Production

Figure 4:
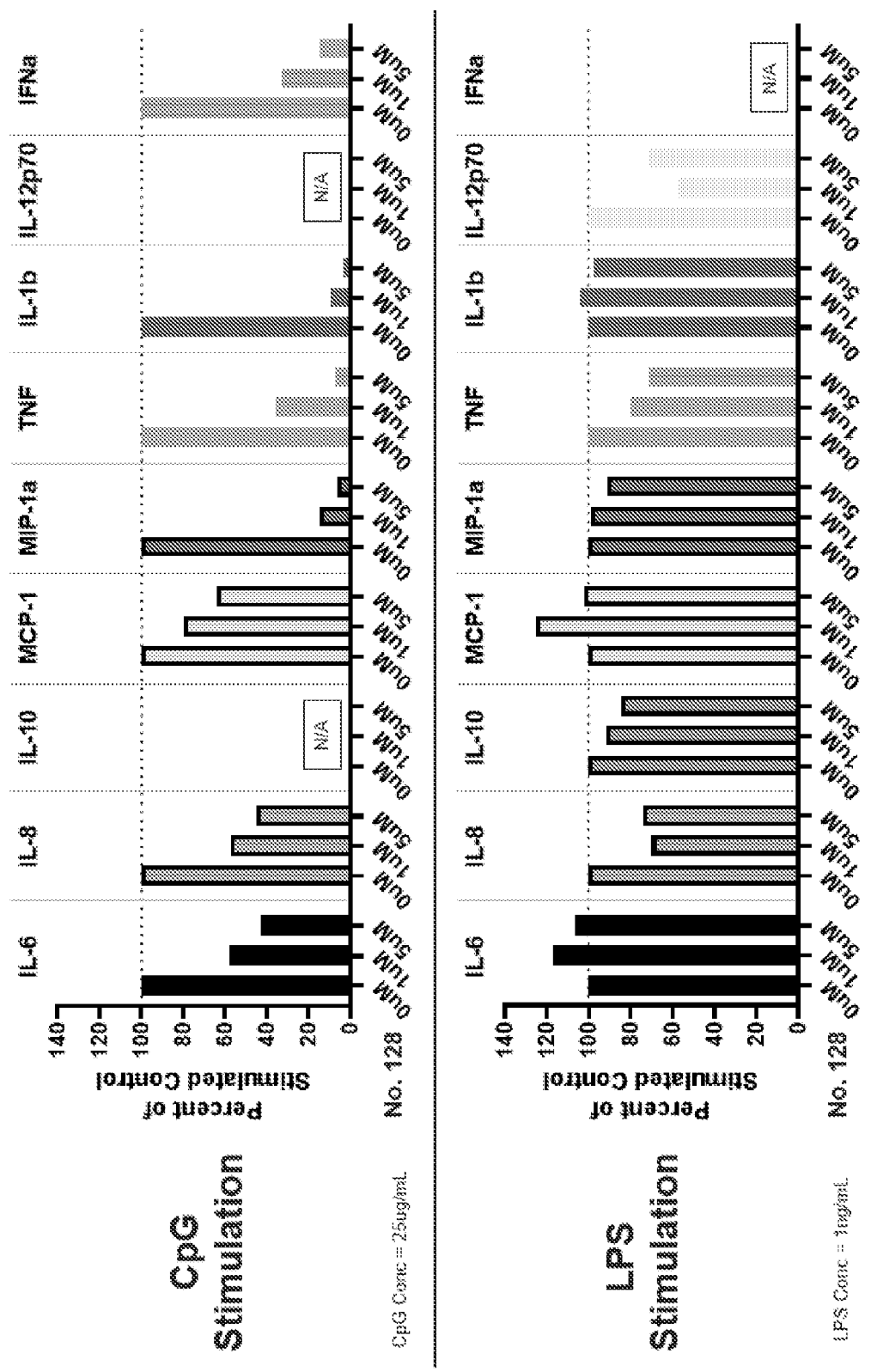
FIG. 4 is a graph showing cytokine and chemokine levels.

The impact on in vitro cytokine production after exposure to Compound No. 128 was assessed in stimulated whole blood following a 24 hour incubation. As shown in FIG. 4, Compound No. 128 decreased cytokine and chemokine production upon cellular stimulation.

The invention claimed is:

1. A method of treating splenomegaly in a human subject in need thereof comprising administering a Bruton's Tyrosine Kinase (BTK) inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof, and the human subject has an accumulation of malignant CD34+ myeloid cells in their spleen.

2. The method of claim 1, wherein the malignant CD34+ myeloid cells have decreased expression of CXCR4 relative to normal myeloid cells.

3. The method of claim 1, wherein the BTK inhibitor is administered in an amount sufficient to stimulate migration of the malignant CD34+ myeloid cells to peripheral blood of the human subject.

4. The method of claim 1, wherein the BTK inhibitor is administered in an amount sufficient to decrease activity of VLA-4 in the malignant CD34+ myeloid cells.

5. The method of claim 1, wherein the BTK inhibitor is administered in an amount sufficient to decrease expression of VLA-4 in the malignant CD34+ myeloid cells.

6. The method of claim 1, wherein the human subject is suffering from myelofibrosis.

7. The method of claim 6, wherein the myelofibrosis is selected from the group consisting of primary myelofibrosis (PMF), post-polycythemia vera myelofibrosis (post PV-MF), and post-essential thrombocythemia myelofibrosis (post ET-MF).

8. The method of claim 1, wherein the human subject did not respond to ruxolitinib therapy.

9. The method of claim 1, wherein the human subject has a JAK2V617F mutation.

10. The method of claim 9, wherein the human subject has acute myeloid leukemia (AML) secondary to a myeloproliferative neoplasm (MPN).

11. The method of claim 1, wherein the human subject does not have a JAK2V617F mutation.

12. The method of claim 11, wherein the human subject has acute myeloid leukemia secondary to a myeloproliferative neoplasm.

13. A method of stimulating migration of malignant CD34+ myeloid cells from hematopoietic tissue to the peripheral blood in a human subject suffering from splenomegaly, comprising administering a BTK inhibitor to the human subject, wherein the BTK inhibitor is 1-(4-(((6-amino-5-(4-phenoxyphenyl)pyrimidin-4-yl)amino)methyl)-4-fluoropiperidin-1-yl)prop-2-en-1-one or a pharmaceutically acceptable salt thereof.

14. The method of claim 13, wherein the human subject has an accumulation of malignant CD34+ myeloid cells in the spleen.

15. The method of claim 13, wherein the malignant CD34+ myeloid cells have decreased expression of CXCR4 relative to normal myeloid cells.

16. The method of claim 13, wherein the human subject is suffering from myelofibrosis.

17. The method of claim 16, wherein the myelofibrosis is selected from the group consisting of primary myelofibrosis (PMF), post-polycythemia vera myelofibrosis (post PV-MF), and post-essential thrombocythemia myelofibrosis (post ET-MF).

18. The method of claim 13, wherein the human subject did not respond to ruxolitinib therapy.

19. The method of claim 13, wherein the human subject has a JAK2V617F mutation.

20. The method of claim 19, wherein the human subject has acute myeloid leukemia (AML) secondary to a myeloproliferative neoplasm (MPN).

21. The method of claim 13, wherein the human subject does not have a JAK2V617F mutation.

22. The method of claim 21, wherein the human subject has acute myeloid leukemia secondary to a myeloproliferative neoplasm.

23. The method of claim 13, wherein the hematopoietic tissue is extramedullary hematopoietic tissue.

24. The method of claim 13, wherein the hematopoietic tissue is bone marrow.

25. The method of claim 13, wherein the hematopoietic tissue is the spleen.

26. The method of claim 13, wherein the hematopoietic tissue is the liver.

27. The method of claim 13, wherein the human subject has not been treated with a JAK2 inhibitor.

28. The method of claim 13, wherein the human subject is intolerant to a JAK2 inhibitor.

29. The method of claim 13, wherein the human subject is ineligible for treatment with a JAK2 inhibitor.

30. The method of claim 13, wherein the human subject is relapsed following JAK2 inhibitor treatment or is refractory to JAK2 inhibitor treatment.

31. The method of claim 13, wherein the BTK inhibitor is administered once daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, 480 mg and 560 mg.

32. The method of claim 13, wherein the BTK inhibitor is administered twice daily at a dose selected from the group consisting of 15 mg, 25 mg, 30 mg, 50 mg, 60 mg, 75 mg, 90 mg, 100 mg, 120 mg, 150 mg, 175 mg, 180 mg, 200 mg, 225 mg, 240 mg, 250 mg, 275 mg, 300 mg, 325 mg, 350 mg, 360 mg, 375 mg, 480 mg and 560 mg.

33. The method of claim 13, wherein the BTK inhibitor is orally administered.

* * * * *